US008741812B2

(12) United States Patent
Javitt

(10) Patent No.: US 8,741,812 B2
(45) Date of Patent: Jun. 3, 2014

(54) CLASS OF STEROL LIGANDS AND THEIR USES IN REGULATION OF CHOLESTEROL AND GENE EXPRESSION

(75) Inventor: Norman B. Javitt, New York, NY (US)

(73) Assignee: New York University, New York, NY (US)

(*) Notice: Subject to any disclaimer, the term of this patent is extended or adjusted under 35 U.S.C. 154(b) by 1497 days.

(21) Appl. No.: 11/212,031

(22) Filed: Aug. 25, 2005

(65) Prior Publication Data

US 2006/0121024 A1 Jun. 8, 2006

Related U.S. Application Data

(60) Provisional application No. 60/548,755, filed on Feb. 27, 2004.

(51) Int. Cl.
  *C40B 30/04* (2006.01)
  *A61K 49/00* (2006.01)
(52) U.S. Cl.
  CPC ...................................... *A61K 49/00* (2013.01)
  USPC ............................................................. 506/9
(58) Field of Classification Search
  CPC .................................................. A61K 49/0004
  USPC ............................................... 514/170; 506/9
  See application file for complete search history.

(56) References Cited

U.S. PATENT DOCUMENTS

| 4,427,668 | A | 1/1984 | Javitt |
| 4,939,134 | A | 7/1990 | Javitt |
| 5,376,652 | A | 12/1994 | Javitt |
| 5,965,449 | A | 10/1999 | Novak |
| 6,562,609 | B1 | 5/2003 | Russell et al. |
| 2004/0121992 | A1 | 6/2004 | Javitt |
| 2005/0038301 | A1 | 2/2005 | Kavtaradze et al. |

OTHER PUBLICATIONS

Pikuleva et al. "Novel sterols synthesized via the CYP27A1 metabolic pathway". Archives of Biochemistry and Biophysics. 2003. vol. 420. pp. 35-39.*
Andersson, S. et al. (1989) J Biol Chem 264:8222-8229.
Araya, Z. et al. (2003) Biochem J 372:529-534.
Best, M.D. et al. (2004) Chembiocem 5(6):811-819.
Bjorkhem, I. et al. (1981) J Lipid Res 22:191-200.
Bjorkhem, I. et al. (2001) J Lipid Res 42:366-371.
Bramlett, K.S. et al. (2003) J. Pharmcol. Exp. Therap 307:291-296.
Cali, J.J. and Russell,D.W. (1991) J Biol Chem 266:7774-7778.
Cao GQ et al. (2003) J Biol. Chem. 278:1131-1136.
Clare, K. et al. (1995) Atherosclerosis 118:67-75.
Fu, X. et al. (1991) J Biol Chem 276:38378-38387.

(Continued)

*Primary Examiner* — Benjamin Packard
(74) *Attorney, Agent, or Firm* — Klauber & Jackson LLC

(57) ABSTRACT

This invention relates to novel physiological oxysteroids and oxysteroid hormones which are C27 modified sterols, particularly derivatives of intermediates in cholesterol synthesis, including lanosterol, zymosterol and desmosterol, including C27 diol and C27 acid derivatives, as well as related compounds and analogs thereof. The invention relates to treatment of cholesterol-related conditions by modulating the rate of cholesterol synthesis or cholesterol metabolism by administration of the oxysteroids, analogs or antagonists thereof. Methods are provided for ameliorating, treating or preventing macular degeneration by administering an agent which stimulates the expression or activity of steroid sulphotransferase (SLUT2), particularly SLUT2B1b, or which stimulates the expression or activity of CYP27A1 or sterol 27-hydroxylase. Assays for identification of analogs, antagonists or modulators of the oxysteroids or of sterol 27-hydroxylase are provided.

4 Claims, 7 Drawing Sheets

(56) References Cited

OTHER PUBLICATIONS

Fuda H. et al. (2002) J. Biol. Chem. 277(39):36161-36166.
Her, C. et al. (1998) Genomics 53:284-295.
Honda, A. et al. (1999) J Lipd Res 40:1520-1528.
Hoppe, G. et al. (2001) Invest Ophthalmol Vis Sci 42:2714-2720.
Janowski BA et al. (1996) Nature 383:728-731.
Janowski et al. (1999) Proc. Natl. Acad. Sci. USA 96:266-271.
Javitt, N. B. (2000) Biochim Biophys Acta. 1529:136-141.
Javitt, NB et al. (2001) Endrocrinology 142(7):2978-2984.
Joseph et al. (2002) Proc. Natl. Acad. Sci. USA 99:7604-7609.
Joseph SB et al. (2003) Nat Med 9:213-219.
Langmann, T. et al. (2005) Biochem et Biophys Acta 1740(2):155-161.
Llirbat, B. et al. (1997) Journal of Lipid Research vol. 38 pp. 22-34.
Lobaccaro, J.M. et al. (2001) Ann Endocrinol (Paris) 62:239-247.
Lu, T.T. et al. (2001) J. Biol. Chem. 276:37735-37738.
Naseem, S.M. and Heald, F.P. (1987) Biochem Int 14:71-84.
Ohtani, K. et al. (1996) Biosci Biotechnol Biochem 60:1989-1993.
Quinn, C.M. et al. (2005) Biochem J 385(Pt 3):823-830.
Rao CV et al (2002) Cancer Det and Prev 26(6):4756.
Rodriguez, I.R. et al. (2004) Investig Ophthalmol and Vis Sci 45(8):2830-2837.
Santillan, G. et al. (1980) Atherosclerosis 35:1-10.
Sever, N. et al. (2003) J Biol Chem 278(52):52579-52490.
Song C. and Liao, S. (2000) Endocrinology 141:4180-4184.
Song, B-L and DeBose-Boyd RA (2004) J. Biol. Chem. 279(27):28798-28806.
Sonoda, Y. (1988) Chem. Pharm. Bull. 36(3):966-973.
Verrips, A. et al. (2000) Brain 123(pt 5):908-919.
Wassif, C.A. et al. (2003) Steroids 68(6):497-502.
Weiss JF et al. (1976) Arch Neurology 33(3):180.

\* cited by examiner

CLASS OF STEROL LIGANDS AND THEIR USES IN REGULATION OF CHOLESTEROL AND GENE EXPRESSION

CROSS REFERENCE TO RELATED APPLICATIONS

The present application is a Continuation-in-Part of co-pending PCT Application No. PCT/US05/005945 filed Feb. 25, 2005, which in turn, claims priority from U.S. Provisional Application Ser. No. 60/548,755, filed Feb. 27, 2004. Applicants claim the benefits of 35 U.S.C. §120 as to the PCT application and priority under U.S.C. §119(e) as to said United States Provisional application, and the entire disclosures of all of which applications are incorporated herein by reference in their entireties.

GOVERNMENTAL SUPPORT

The research leading to the present invention was supported, at least in part, by grants from the United States Health Service Grant No. HL66304. Accordingly, the Government may have certain rights in the invention.

FIELD OF THE INVENTION

This invention relates to oxysteroids and oxysteroid hormones which have been identified. These oxysteroids are C27 modified sterols. Included in the invention are derivatives of intermediates in cholesterol synthesis, including lanosterol, zymosterol and desmosterol, including C27 diol and C27 acid derivatives, as well as related compounds and analogs thereof. The oxysteroids are capable of binding to or otherwise interacting with orphan nuclear receptors to result in modulation of gene expression. The invention further relates to methods of modulating the rate of cholesterol synthesis in a mammal and treatment of cholesterol-related conditions. The invention includes methods for ameliorating, treating or preventing macular degeneration in a mammal comprising administering to said mammal an agent which stimulates or enhances the expression or activity of CYP27A1 or sterol 27-hydroxylase, or of hydroxysteroid sulfotransferase or SLUT2B1b. In a further aspect, a method is provided for ameliorating, treating or preventing macular degeneration in a mammal comprising increasing the 27-hydroxylation or sulfonation of cholesterol intermediates, including 7-ketocholesterol.

BACKGROUND OF THE INVENTION

Cholesterol is the major steroid constituent of animal tissue, and an essential component of plasma and cell membranes. Cholesterol is a 3-hydroxy sterol having a perhydro-1,2-cyclopenenophenanthrene ring system and an aliphatic side chain at position 17. Because it is insoluble in body fluids, cholesterol must be transported through the bloodstream by carriers such as low-density lipoprotein (LDL).

Cholesterol is an extremely important biological molecule that has roles in membrane structure as well as being a precursor for the synthesis of the steroid hormones and bile acids.

The synthesis and utilization of cholesterol must be tightly regulated in order to prevent over-accumulation and abnormal deposition within the body. Of particular importance clinically is the abnormal deposition of cholesterol and cholesterol-rich lipoproteins in the coronary arteries. Such deposition, eventually leading to atherosclerosis, is the leading contributory factor in diseases of the coronary arteries.

A portion of the cholesterol in the body derives from biosynthesis de novo. In the process of generating cholesterol, lanosterol is the first sterol formed and conversion to cholesterol requires at least a dozen additional steps.

Through a series of reactions, lanosterol is converted to cholesterol (FIG. 1). The conversion of lanosterol, through zymosterol, and desmosterol, including several intermediates is depicted in FIG. 2.

Normal healthy adults synthesize cholesterol at a rate of approximately 1 g/day and consume approximately 0.3 g/day. A relatively constant level of cholesterol in the body (150-200 mg/dL) is maintained primarily by controlling the level of de novo synthesis. The level of cholesterol synthesis is regulated in part by the dietary intake of cholesterol. Cholesterol from both diet and synthesis is utilized in the formation of membranes and in the synthesis of the steroid hormones and bile acids (see below). The greatest proportion of cholesterol is used in bile acid synthesis.

Excessive accumulation of cholesterol has been implicated as the primary causative factor in a number of diseases, including atherosclerosis, which is characterized by an abnormal hardening and thickening of the arterial walls due to the accumulation and deposition of fatty materials, including cholesterol. This can lead to thrombosis and infarction.

The cholesterol metabolite 26-hydroxycholesterol, now known as 27-hydroxycholesterol, has been previously shown to be associated with cholesterol synthesis (U.S. Pat. No. 4,427,668). More specifically, a reduced level of 27-hydroxycholesterol in the serum was found to be associated with cholesterol build up in the tissues; thus, the administration of 27-hydroxycholesterol was proposed as a method for reducing the rate of cholesterol synthesis in the body. Thereafter, as disclosed in U.S. Pat. No. 4,939,134, it was discovered that 27-amino cholesterol and certain amino-substituted analogs and derivates were more potent inhibitors of cholesterol synthesis and accumulation than 27-hydroxycholesterol. 27-hydroxycholesterol was later found to be effective in reducing the occurrence of restenosis following injury to the blood vessels lumen (U.S. Pat. No. 5,376,652). Individuals with a genetic defect in producing 27-hydroxycholesterol exhibit accelerated atherosclerosis and die early in life of severe coronary artery disease. The molecular basis of this genetic disease is a mutation in the CYP 27 gene, which results in a lack of cholesterol 27-hydroxylase activity.

The term "oxysterol", although not precisely defined, refers generically to derivatives of cholesterol having one, or occasionally more, hydroxyl or oxo groups, in addition to the 3β-OH group of cholesterol (Russell, D. W. (2000) Biochim Biophys Acta. 1529:126-135; Javitt, N. B. (2000) Biochim Biophys Acta. 1529:136-141). For the most part these "oxysterols", such as 27-hydroxycholesterol and 24s-hydroxycholesterol, are endogenously-derived derivatives of cholesterol. Others such as 25-hydroxycholesterol, which can be generated endogenously (Lund, E. G. et al. (1998) J. Biol. Chem. 273:34316-34327), are also well-known oxidation products.

Kandutsch et al. reported that oxygenated cholesterol has an inhibitory effect on the proliferation of fibroblasts and lymphocytes in vitro, perhaps by inhibiting hydroxymethylglutaryl coenzyme A reductase (HMG CO-A reductase), the rate-limiting enzyme in cholesterol biosynthesis (Kandutsch et al. (1978) Science 201:498). The inhibitory effect by oxysterols on vascular smooth muscle cells has been suggested to be a toxic effect (Zhou et al. (1993) Proc. Soc. Exp. Biol. Med. 202: 75-80).

It is now well established that one of the basic mechanisms for regulating gene expression is via the binding of "oxysterols" to nuclear receptors that in turn modulate gene expression by affecting their promoter region (Lu, T. T. et al. (2001) J. Biol. Chem. 276:37735-37738; Lobaccaro, J. M. et al. (2001) Ann Endocrinol (Paris) 62:329-247). These nuclear receptors are often referred to as "orphan" nuclear receptors, with the term "orphan" referring to their status before known oxysterols were identified that bind to these receptors to modulate both their expression and the genes with appropriate target promoter regions. The oxysterols 24,25-epoxy cholesterol, 25-hydroxycholesterol and 27-hydroxycholesterol are now known to function as ligands for nuclear receptors that modulate other determinants of cholesterol homeostasis (Janowski et al. (1996) Nature 383:728-31). The oxysterol 25R,26-hydrocholesterol (also referred to as 27-hydroxycholesterol) appears to have a role in preventing cholesterol accumulation in arteries. Although oxysterols can function as ligands for nuclear receptors, they can also have biological activities unrelated to this function. Bramlett et al. recently discussed a natural product ligand of the oxysterol receptor LXR, the fungal metabolite paxilline (Bramlett, K. S. et al. (2003) J. Pharmcol Exp. Therap 307:291-296).

Therefore, in view of the fact that macronutrients and metabolites, including endogenous sterols, affect gene expression through nuclear receptors as well as directly influence metabolic processes, there exists a need in the art for novel ligands for these receptors and modulators of these processes. Furthermore, there exists a need for additional approaches to controlling and modulating cholesterol levels and endogenous sterol constituents.

The citation of references herein shall not be construed as an admission that such is prior art to the present invention.

SUMMARY OF THE INVENTION

Based initially on our studies of children with Smith-Lemli-Opitz syndrome (Wassif, C. A. et al. (2003) Steroids 68(6):497-502) and more recently utilizing the enzyme CYP27A1, we have identified the existence of a new class of oxysterol ligands, generated from intermediates in cholesterol synthesis. The novel receptor ligands provided herein have novel biologic activities relating to modified gene expression occurring in the pathogenesis of disease.

Smith-Lemli-Opitz syndrome (SLOS) is a genetically determined disease resulting from a mutation in the gene encoding the 7-dehydrocholesterol 7-reductase (DHC7R) enzyme that converts 7-dehydrocholesterol to cholesterol. Neonates suffering from SLOS have very high levels of 7-dehydrocholesterol in plasma, and a decreased cholesterol synthesis. The compound, 27-hydroxy-7-dehydrocholesterol, has been found to specifically upregulate the expression of the nuclear receptor LXRα, in contrast to 27-hydroxycholesterol that upregulates the expression of the LXRα and LXRβ nuclear receptors.

The invention provides methods of reducing cholesterol accumulation in a subject in need thereof. In one feature, the invention provides a method of reducing cholesterol synthesis. In another feature, the invention provides a method for increasing cholesterol degradation. Both of these features of the invention are described and provided herein.

Studies of the regulation of cholesterol synthesis in Smith-Lemli-Opitz syndrome (SLOS) have led to the discovery of a new metabolic route that generates novel endogenous oxysterol ligands. The work described below describes the identification of members of this new class of oxysterols which can be derived from precursor intermediates in the metabolic pathway for cholesterol synthesis. In particular, the invention identifies further oxysterols, particularly C27 metabolites of lanosterol, zymosterol and desmosterol and other sterol intermediates in the pathway from squalene to cholesterol. The invention contemplates that these C27 metabolites can be generated in vivo endogenously by CYP27A1. In particular, it has been discovered that lanosterol, zymosterol and desmosterol are substrates for the ubiquitous mitochondrial enzyme P450 CYP27A1 enzyme sterol 27-hydroxylase. These novel oxysterols and C27 sterols with similar or related structures, particularly analogs or antagonists thereof, are useful as novel ligands for modification of gene expression or modulation of cholesterol metabolism, synthesis and cholestatic disease. Further, the modulation of the amount or generation of these C27 metabolites by administration of agonists, antagonists or by manipulation or modification of sterol 27-hydroxylase on these intermediates and their derivatives can be used in modification of gene expression, including in providing or modulating ligands of orphan nuclear receptors, or modulation of cholesterol metabolism, synthesis and cholestatic disease. In particular, these novel oxysterols and sterols with similar or related structures, particularly analogs thereof, may have pathophysiological effects and it is therefore contemplated to reduce their amount or antagonize or otherwise block or modulate their effects, including their modification of gene expression. For instance, it has been discovered that 27-hydroxylation of cholesterol intermediates may alter their activity, including any such activity which is associated or correlated with disease. In one such instance, stimulation or induction of CYP27A1 and/or 27-hydroxylation of cholesterol intermediates or endogenous steroid compounds is contemplated and provided herein to reduce or treat disease. In particular, 27-hydroxylation of 7-ketocholesterol, or stimulation of CYP27A1 is provided for the alleviation, treatment or reduction of adult macular degeneration.

It has been recognized that these novel oxysterols and C27 sterols are capable of stimulating ubiquitination of proteins, particularly including the enzyme HMG CoA reductase. Ubiquitination targets or otherwise initiates subsequent degradation of proteins. HMG CoA reductase catalyzes the production of mevalonate, a rate controlling step in cholesterol synthesis. Thus, the novel oxysterols and C27 sterols of the present invention are contemplated as having a role in modulation of cholesterol synthesis and metabolism and in the maintenance of cholesterol and lipids in vivo. Modulation of these C27 sterols provides a means to modulate or otherwise control the synthesis and metabolism of cholesterol and proteins involved in the cholesterol pathway. In addition, manipulation of these novel oxysterols and C27 sterols may result in manipulation of ubiquitination and/or degradation of proteins involved in sterol synthesis and lipid metabolism and other metabolic pathways.

One feature of the invention is based on the identification of C27 metabolites or derivatives of intermediates in cholesterol synthesis, particularly including lanosterol, zymosterol and desmosterol.

One feature of the invention is directed to methods that modulate cholesterol accumulation, endogenous sterol constituents and/or lipid metabolism in a subject by providing methods that alter cholesterol synthesis or metabolism. Accordingly, the invention features a therapeutic method of modulating cholesterol synthesis in a subject in need thereof, comprising administering a therapeutically effective amount of therapeutic agent selected from: C27 metabolite or derivative of cholesterol intermediates or endogenous steroids, C27 metabolite or derivative of lanosterol, zymosterol or desmosterol, agents which mimic or are analogs of C27 metabolites or derivatives of lanosterol, zymosterol or desmosterol, agents able to act as antagonists of C27 metabolites or derivatives of lanosterol, zymosterol or desmosterol, sterols which have the formula Formula 1, agents which promote or prevent expression and/or activity of sterol 27-hydroxylase, agents which modulate the activity of sterol 27-hydroxylase, agents which modulate the expression of CYP27A1, antibodies able to bind to or recognize C27 metabolites or derivatives of lanosterol, zymosterol or desmosterol, antibodies able to inhibit the activity of C27 metabolites or derivatives of lanosterol, zymosterol or desmosterol, wherein cholesterol synthesis is modulated, altered or reduced.

The invention thus relates to sterols of the formula:

FORMULA 1

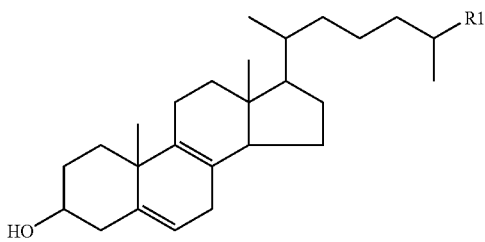

wherein R1 is selected from $CH_3$, $CH_2OH$, COOH, CO, CS, $CH_2$, CH, CHO;

or a pharmaceutically acceptable salt, solvate or prodrug thereof and isomers and stereoisomers thereof.

In a more specific embodiment, lanosterol-27 diol is administered. In another specific embodiment, zymosterol-27 diol is administered. In another specific embodiment, desmosterol-27 diol is administered. In another specific embodiment, two or more of lanosterol-27 diol, zymosterol-27 diol and desmosterol-27 diol are administered together.

In an additional specific embodiment, lanosterol-27 acid is administered. In another specific embodiment, zymosterol-27 acid is administered. In another specific embodiment, desmosterol-27 acid is administered. In another specific embodiment, two or more of lanosterol-27 acid, zymosterol-27 acid and desmosterol-27 acid are administered together.

In a still further embodiment, sterols which have the formula Formula 1 are administered.

In an additional embodiment, the invention provides methods of modulating nuclear orphan receptors comprising administering a therapeutically effective amount of therapeutic agent selected from: C27 metabolite or derivative of lanosterol, zymosterol or desmosterol, agents which mimic or are analogs of C27 metabolites or derivatives of lanosterol, zymosterol or desmosterol, agents able to act as antagonists of C27 metabolites or derivatives of lanosterol, zymosterol or desmosterol, sterols which have the formula Formula 1, agents which promote or prevent expression and/or activity of sterol 27-hydroxylase, agents which modulate the activity of sterol 27-hydroxylase, agents which modulate the expression of CYP27A1, antibodies able to bind to or recognize C27 metabolites or derivatives of lanosterol, zymosterol or desmosterol, antibodies able to inhibit the activity of C27 metabolites or derivatives of lanosterol, zymosterol or desmosterol.

In a further aspect, the invention provides methods of modulating gene expression comprising administering a therapeutically effective amount of therapeutic agent selected from: C27 metabolite or derivative of lanosterol, zymosterol or desmosterol, agents which mimic or are analogs of C27 metabolites or derivatives of lanosterol, zymosterol or desmosterol, agents able to act as antagonists of C27 metabolites or derivatives of lanosterol, zymosterol or desmosterol, sterols which have the formula Formula 1, agents which promote or prevent expression and/or activity of sterol 27-hydroxylase, agents which modulate the activity of sterol 27-hydroxylase, agents which modulate the expression of CYP27A1, antibodies able to bind to or recognize C27 metabolites or derivatives of lanosterol, zymosterol or desmosterol, antibodies able to inhibit the activity of C27 metabolites or derivatives of lanosterol, zymosterol or desmosterol.

In a still further aspect, the invention provides a method for ameliorating, treating or preventing macular degeneration comprising modulating the expression or activity of CYP27A1 or sterol 27-hydroxylase. In one such aspect, a method is provided for ameliorating, treating or preventing macular degeneration in a mammal comprising administering to said mammal an agent which stimulates or enhances the expression or activity of CYP27A1 or sterol 27-hydroxylase. In a further aspect, a method is provided for ameliorating, treating or preventing macular degeneration in a mammal comprising increasing the 27-hydroxylation of cholesterol intermediates. A method is provided for ameliorating, treating or preventing macular degeneration in a mammal comprising increasing the 27-hydroxylation of 7-ketocholesterol in said mammal. In one such method, 27-hydroxyl-7-ketocholesterol is administered. In a further such aspect, a method is provided for ameliorating, treating or preventing macular degeneration in a mammal comprising administering to said mammal an agent which stimulates or enhances the expression or activity of hydroxysteroid sulphotransferase, particularly SULT2, particularly SULT2B1b. In a further aspect, a method is provided for ameliorating, treating or preventing macular degeneration in a mammal comprising increasing the sulfonation of cholesterol intermediates. A method is provided for ameliorating, treating or preventing macular degeneration in a mammal comprising increasing the sulfonation of 7-ketocholesterol in said mammal. In one such method, 7-ketocholesterol-3-sulfate is administered.

In another embodiment of the method of the invention, a nucleic acid encoding a peptide or protein inhibitor of sterol 27-hydroxylase is administered, and in a related embodiment, an antisense sequence or catalytic RNA capable of interfering with the expression of sterol 27-hydroxylase is administered. In further embodiments, inhibition of sterol 27-hydroxylase activity is achieved with a combination of these approaches.

The invention provides a screening method for identifying agent compounds capable of modulating the activity of C27 metabolites or derivatives of lanosterol, zymosterol or desmosterol or analogs thereof, comprising measuring the activity of a C27 metabolite or derivative of lanosterol, zymosterol or desmosterol or analogs thereof in the presence of a test compound, wherein a compound which modulates said activity relative to a control is identified as a compound capable of modulating or altering the activity of C27 metabolite or derivative of lanosterol, zymosterol or desmosterol or analogs thereof.

In a further aspect, the invention features a screening method for identifying agent compounds capable of inhibiting the activity of C27 metabolites or derivatives of lanosterol, zymosterol or desmosterol or analogs thereof, comprising measuring the activity of a C27 metabolite or derivative of lanosterol, zymosterol or desmosterol or analogs thereof in the presence of a test compound, wherein a compound which reduces said activity relative to a control is identified as a compound capable of inhibiting the activity of C27 metabolite or derivative of lanosterol, zymosterol or desmosterol or analogs thereof.

In a further aspect, the invention features a screening method for identifying agent compounds capable of activating or enhancing the activity of C27 metabolites or derivatives of lanosterol, zymosterol or desmosterol or analogs thereof, comprising measuring the activity of a C27 metabolite or derivative of lanosterol, zymosterol or desmosterol or analogs thereof in the presence of a test compound, wherein a compound which activates or enhances said activity relative to a control is identified as a compound capable of activating or enhancing the activity of C27 metabolite or derivative of lanosterol, zymosterol or desmosterol or analogs thereof.

In a further aspect, the invention features a screening method for identifying agent compounds capable of mimicking the activity of C27 metabolites or derivatives of lanosterol, zymosterol or desmosterol or analogs thereof, comprising screening for or measuring a known activity of a C27 metabolite or derivative of lanosterol, zymosterol or desmosterol or analog thereof in the presence of a test compound, wherein a compound which mimics said activity relative to a control is identified as a compound capable of mimicking the activity of C27 metabolite or derivative of lanosterol, zymosterol or desmosterol or analogs thereof. In one such aspect cholesterol synthesis is measured. In an additional such aspect, the activity of a gene ordinarily activated in the presence of said ligand C27 metabolite or derivative of lanosterol, zymosterol or desmosterol or analog thereof.

In one embodiment, compounds that modulate the activity or expression of C27 metabolites or derivatives of lanosterol, zymosterol or desmosterol or analogs thereof, including antagonists thereof, are identified in a cell-free assay system. In another embodiment, compounds that modulate the activity or expression of C27 metabolites or derivatives of lanosterol, zymosterol or desmosterol or analogs thereof are identified in a cell-based assay system. In another embodiment, agents that modulate the expression, activity or both the expression and activity of C27 metabolites or derivatives of lanosterol, zymosterol or desmosterol or analogs thereof are identified in an animal model.

The invention further provides pharmaceutical compositions useful in the therapeutic method of the invention. More specifically, the invention features a pharmaceutical composition comprising purified C27 metabolites or derivatives of lanosterol, zymosterol or desmosterol or analogs or antagonists thereof and a pharmaceutically acceptable carrier. In another embodiment, the invention features a pharmaceutical composition comprising purified lanosterol-27 diol, and a pharmaceutically acceptable carrier. In another embodiment, the invention features a pharmaceutical composition comprising purified lanosterol-27 acid, and a pharmaceutically acceptable carrier. In another embodiment, the invention features a pharmaceutical composition comprising purified zymosterol-27 diol, and a pharmaceutically acceptable carrier. In another embodiment, the invention features a pharmaceutical composition comprising purified zymosterol-27 acid, and a pharmaceutically acceptable carrier. In another embodiment, the invention features a pharmaceutical composition comprising purified desmosterol-27 diol, and a pharmaceutically acceptable carrier. In another embodiment, the invention features a pharmaceutical composition comprising purified desmosterol-27 acid, and a pharmaceutically acceptable carrier. In another embodiment, the invention features a pharmaceutical composition comprising purified sterols which have the formula Formula 1, and a pharmaceutically acceptable carrier. In yet another embodiment, the invention features a pharmaceutical composition comprising two or more of lanosterol-27 diol, lanosterol-27 acid, zymosterol-27 diol, zymosterol-27 acid, desmosterol-27 diol, desmosterol-27 acid and sterols which have the formula Formula 1, and a pharmaceutically acceptable carrier.

The invention includes an assay system for screening of potential drugs effective to modulate oxysteroid activity, particularly the activity of target mammalian cells or target genes in cells by interrupting or potentiating the C27 metabolites or derivatives of lanosterol, zymosterol or desmosterol or analogs thereof. In one instance, the test drug could be administered to a cellular sample with the C27 metabolites or derivatives of lanosterol, zymosterol or desmosterol or analogs thereof, or an extract containing the C27 metabolites or derivatives of lanosterol, zymosterol or desmosterol or analogs thereof, to determine its effect upon the activity of the C27 metabolites or derivatives of lanosterol, zymosterol or desmosterol or analogs thereof, or a target gene in cells, by comparison with a control.

Other objects and advantages will become apparent to those skilled in the art from a review of the following description which proceeds with reference to the following illustrative drawings.

The most prominent peak, m/z=437 represents simultaneous loss of the silyl ether+a methyl group and may prove useful for detecting the presence of the metabolite in biologic fluids.

Figure 5:
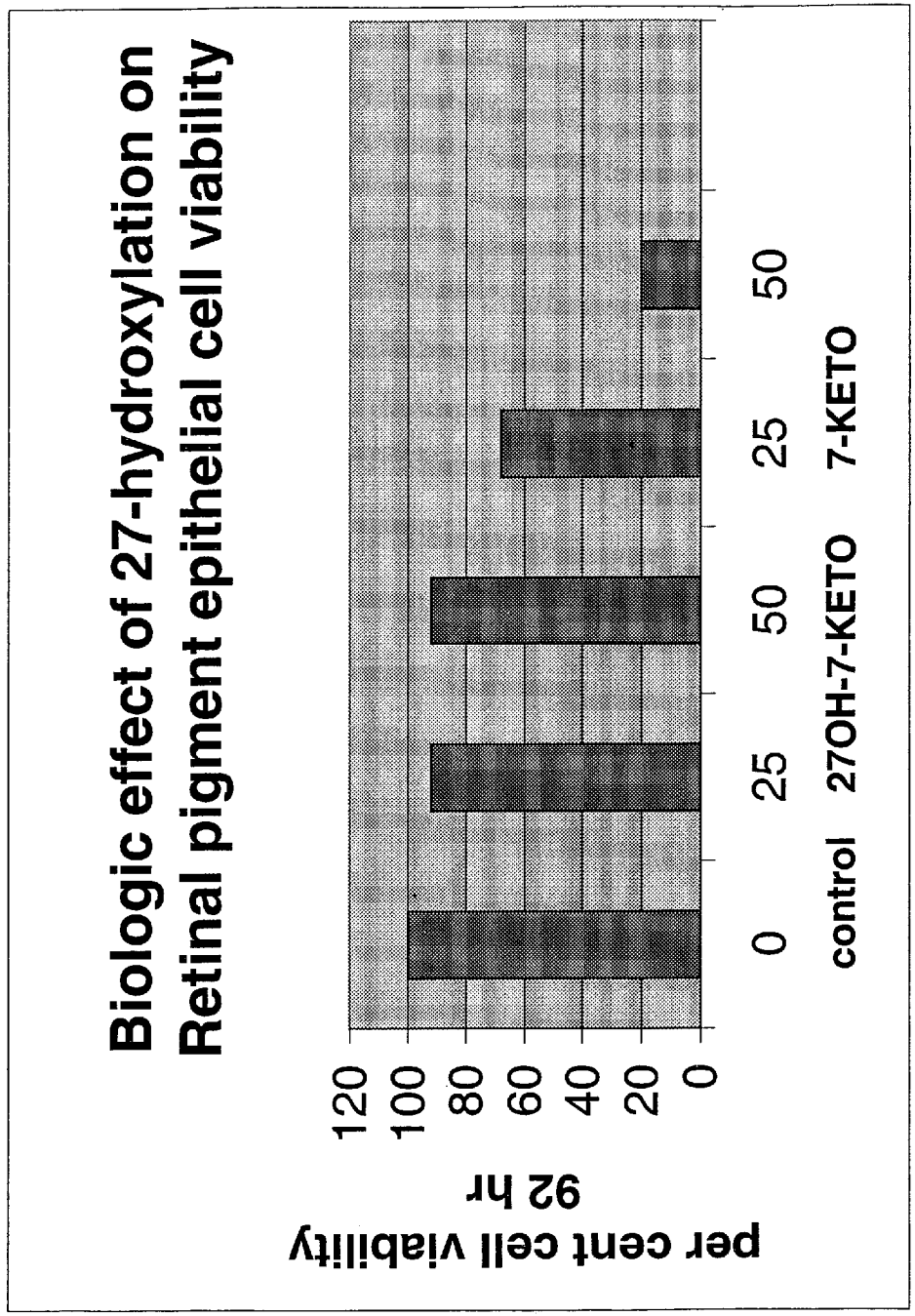

FIG. 5 depicts percent cell viability of retinal pigment epithelial cells in the presence of varying amounts (25 µM and 50 µM) 27-hydroxy-7-ketocholesterol or 7-ketocholesterol.

Figure 6:
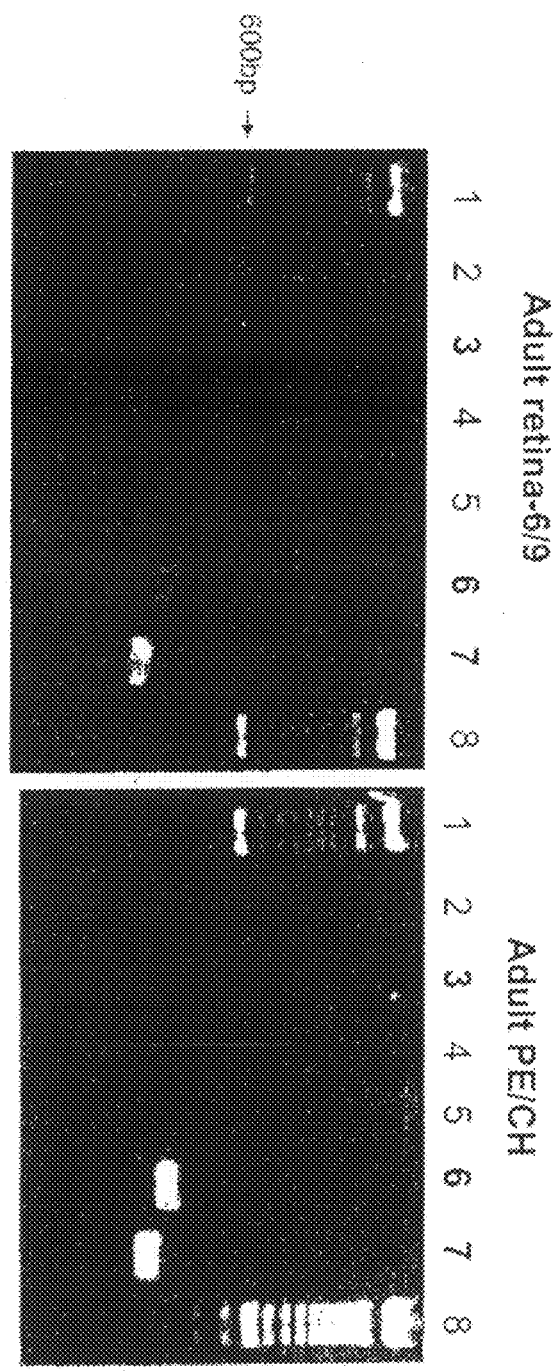

FIG. 6 depicts RT-PCR for various apoproteins in adult human retina and adult PE/CH (pigment epithelium/choroids). Lanes 1 and 8 are markers. Apoproteins are as follows: Lane 2—ApoE, Lane 3—ApoA1, Lane 4—ApoA2, Lane 5—ApoA4, Lane 6—Cyp27A1, Lane 7—GAPDH control.

Figure 7:
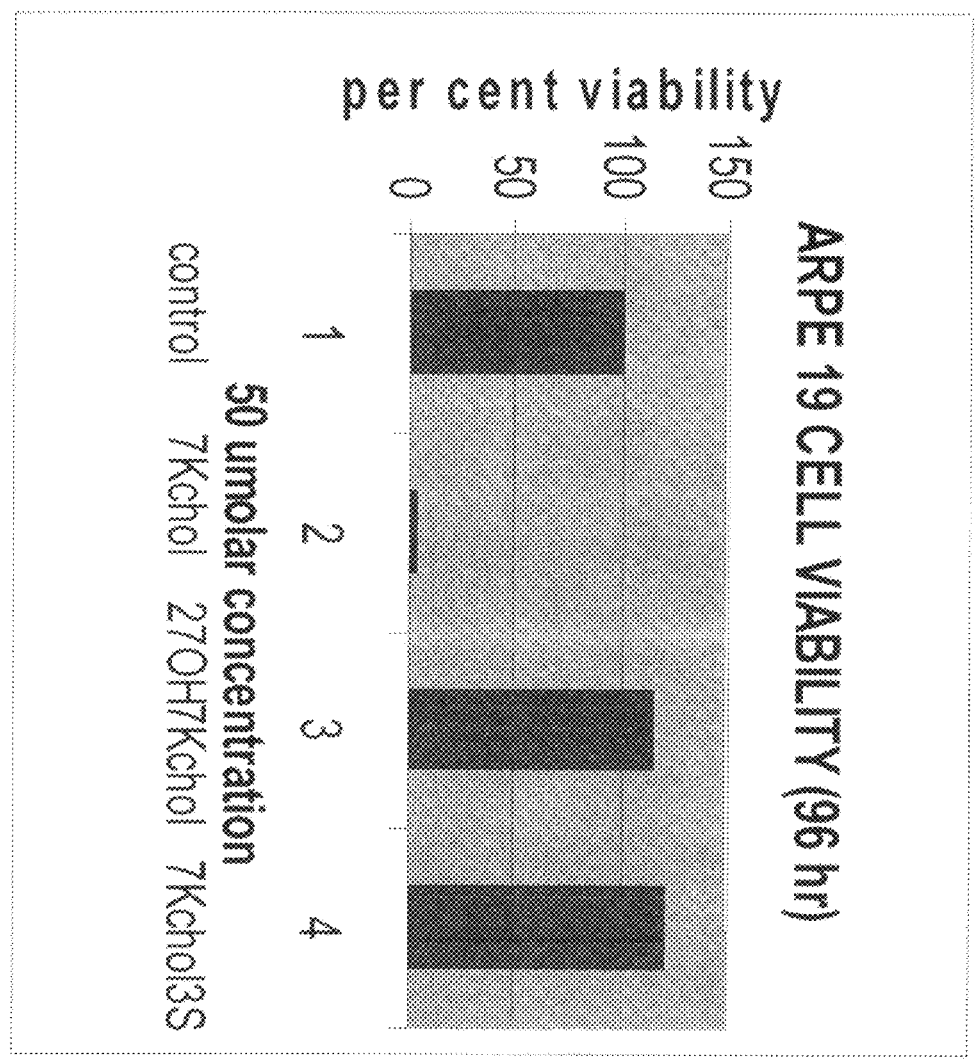

FIG. 7 depicts percent cell viability of retinal pigment epithelial cells in the presence of 50 µM 7-ketocholesterol, 27-hydroxy-7-ketocholesterol or 3-sulfate-7-ketocholesterol.

DETAILED DESCRIPTION

Before the present methods and treatment methodology are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

DEFINITIONS

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules can be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and can be produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

"Treatment" refers to the administration of medicine or the performance of medical procedures with respect to a patient, for either prophylaxis (prevention) or to cure the infirmity or malady in the instance where the patient is afflicted.

The phrase "pharmaceutically acceptable" refers to molecular entities and compositions that are physiologically tolerable and do not typically produce an allergic or similar untoward reaction, such as gastric upset, dizziness and the like, when administered to a human.

A "therapeutically effective amount" is an amount of a reagent or agent sufficient to decrease or prevent the symptoms associated with the disorder being treated or ameliorated. In the case of elevated cholesterol, a therapeutically effective amount refers to an amount sufficient to reduce cholesterol levels in an individual or patient being administered the reagent or agent to a statistically significant extent, for instance by at least 5 percent, by at least 10 percent, at least 20 percent relative to the cholesterol level in the absence of the reagent or agent. The phrase "therapeutically effective amount" is used herein to further mean an amount sufficient to prevent, and preferably reduce by at least about 30 percent, more preferably by at least 50 percent, most preferably by at least 90 percent, a clinically significant change in the S phase activity of a target cell or cellular mass, or other feature of pathology such as for example, gene expression or a physiological feature such as elevated blood pressure, fever or white cell count as may attend its presence and activity.

The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's metabolic system or immune system to utilize the active ingredient, and degree of sterol capacity or modulation thereof desired. Precise amounts of active ingredient required to be administered depend on the judgment of the practitioner and are peculiar to each individual.

As used herein, "pg" means picogram, "ng" means nanogram, "ug" or "μ" mean microgram, "mg" means milligram, "ul" or "μl" mean microliter, "ml" means milliliter, "l" means liter.

General Description

Studies of the regulation of cholesterol synthesis in Smith-Lemli-Opitz (SLOS) syndrome have led to the identification of a new class of oxysterols that circulate in plasma and are derived from precursor intermediates in the metabolic pathway for cholesterol synthesis. Specifically, the 27-hydroxy metabolites of 7- and 8-dehydrocholesterol (7-DHC and 8-DHC) were identified as potent inhibitors of cholesterol synthesis. The present invention now identifies further oxysterols, particularly C27 metabolites of lanosterol, zymosterol and desmosterol and other sterol intermediates in the pathway from squalene to cholesterol. The invention contemplates that these C27 metabolites can be generated in vivo endogenously by CYP27A1. In particular, it has been discovered that lanosterol, zymosterol and desmosterol are substrates for the ubiquitous mitochondrial enzyme P450 CYP27A1 enzyme sterol 27-hydroxylase. These novel oxysterols and C27 sterols with similar or related structures, particularly analogs thereof, are useful as novel ligands for modification of gene expression or modulation of cholesterol metabolism, synthesis and cholestatic disease. Further, the modulation of the amount or generation of these C27 metabolites by administration of agonists, antagonists or by manipulation or modification of sterol 27-hydroxylase on these intermediates and their derivatives can be used in modification of gene expression, including in providing or modulating ligands of orphan nuclear receptors, or modulation of cholesterol metabolism, synthesis and cholestatic disease.

It has been recognized that these novel oxysterols and C27 sterols are capable of stimulating ubiquitination of proteins, particularly including the enzyme HMG CoA reductase. Ubiquitination targets or otherwise initiates subsequent degradation of proteins. HMG CoA reductase catalyzes the production of mevalonate, a rate controlling step in cholesterol synthesis. Thus, the novel oxysterols and C27 sterols of the present invention are contemplated as having a role in modulation of cholesterol synthesis and metabolism and in the maintenance of cholesterol and lipids in vivo. Modulation of these C27 sterols provides a means to modulate or otherwise control the synthesis and metabolism of cholesterol and proteins involved in the cholesterol pathway. In addition, manipulation of these novel oxysterols and C27 sterols may result in manipulation of ubiquitination and/or degradation of proteins involved in sterol synthesis and lipid metabolism and other metabolic pathways. Since cholesterol and lipids are essential in membrane formation and cell growth, and further in as much as ubiquitination is a recognized part of control of proteins, feedback and even implicated in cell growth and cell death mechanisms, the manipulation of these novel oxysterols and C27 sterols may be applied to cell growth, including ion modulation, alleviation, or therapy of conditions of accelerated, aberrant or abnormal cell growth, including cancer and other proliferative diseases and conditions.

In addition to their potent effect on cholesterol synthesis, this new class of oxysterol metabolites and analogs or antagonists thereof, can function as ligands for nuclear receptors that modulate gene expression, including genes involved in cholesterol homeostasis. Thus, the nuclear receptors LXRα and LXRβ have been implicated in the control of cholesterol and fatty acid metabolism in multiple cell type. LXRα is expressed primarily in liver, intestine, adipose tissue, and macrophages, whereas LXRβ is expressed in may cell types (Repa et al. (2000) Annu. Rev. Cell Dev. Biol. 16:459-481). In peripheral cells such as macrophages, LXRs seem to coordinate a physiologic response to cellular cholesterol loading. The physiologic ligands for these receptors have been speculated to include specific intermediates in the cholesterol biosynthetic pathway, such as 24(S), 25-epoxycholesterol (Joseph et al. (2002) Proc. Natl. Acad. Sci. USA 99:7604-7609; Janowski et al. (1999) Proc. Natl. Acad. Sci. USA 96:266-271).

Cholesterol intermediates and their metabolites and derivatives, including oxysterols, play critical roles in regulating cell growth and function and cellular processes. Oxysterols act as regulators in processes including the regulation of bile acid metabolism, control of cell growth, induction of apoptosis, regulation of cholesterol ester formation, effects on LDL receptor levels, induction of cholesterol efflux from cells, induction of differentiation in calcifying vascular cells, formation of foam cells, and activation of nuclear orphan (including LXR) receptors. Oxysterols also have important roles in reverse cholesterol transport, in atherogenesis, and in bile acid and steroid hormone synthesis. The LXR receptors (liver X receptors), LXR and LXR, have oxysterol cholesterol metabolites as their physiological ligands and play a key role in regulation of cholesterol metabolism and transport as well as glucose metabolism and inflammation (Janowski B A et al (1996) Nature 383:728-731; Cao G Q et al (2003) J Biol Chem 278:1131-1136; Joseph S B et al (2003) Nat Med 9:213-219). Modulation of the activity of these receptors may be useful in the treatment of a number of pathophysiological states including dyslipidemia, atherosclerosis and diabetes (Joseph S B et al (2002) Proc Natl Acad Sci USA 99:7604-7609; Cao G Q et al (2003) J Biol Chem 278:1131-1136). Bramlett et al recently described identificatiuon of a nonoxysterol natural product ligand of LXR, the indole alkoid fungal metabolite from *Penicillium paxilli*, paxilline paxilline (Bramlett, K. S. et al. (2003) J. Pharmcol Exp. Therap 307: 291-296).

Additional physiological roles and therapeutic applications of oxysterols and sterol derivatives include in cancer and fertility applications. Rao et al reported that farnesol and lanosterol, given in the diet of rats, significantly suppress colonic aberrant cryptic foci (ACF) formation and crypt multiplicity, suggesting that these agents possess chemopreventive activity against colon carcinogenesis (Rao C V et al (2002) Cancer Det and Prev 26(6):4756). Desmosterol, a possible chemical indicator of brain tumors, is detected in cells of neurogenic, nitrosourea-induced rat tumors (neurinomas and gliomas) and in human astrocytomas grown in lipid-poor media (Weiss J F et al (1976) Arch Neurology 33(3): 180). Additionally, it is recognized that loss of cholesterol is an essential step in the final maturation (capacitation) of human sperm and experimentally maintaining a high level of cholesterol inhibits capacitation. Human sperm also contain much desmosterol, which is also lost during capacitation, and preventing the loss of desmosterol inhibits capacitation (Nimmo M R and Cross N L (2003) Biology of Reprod 68:1308-1317). In a recent report, transgenic mice with a targeted disruption of the Dhcr24 gene encoding desmosterol reductase were evaluated. These mice cannot convert desmosterol to cholesterol and therefore desmosterol accounts for 99% of total sterol. Dhcr24 –/– mice survive, although with poorer growth characteristics, and have degenerated testes and both males and females are sterile (Wechsler A et al (2003) Science 302(19):2087).

Macular degeneration, often called AMD or ARMD (for age-related macular degeneration), is the leading cause of vision loss and blindness in Americans aged 65 and older. Because older people represent an increasingly larger percentage of the general population, vision loss associated with AND is a growing problem. AND is a degenerative condition of the macula, which is the part of the retina responsible for the sharp, central vision needed to read or drive. Because AND affects the macula, central vision loss may occur. Macular degeneration is diagnosed as either dry (non-neovascular) or wet (neovascular). The dry form is more common than the wet, with about 85%-90% of AMD patients diagnosed with dry AND. The wet form of the disease usually leads to more serious vision loss.

Macular degeneration produces a slow, or rarely, sudden painless loss of vision. Early signs of vision loss associated with AND can include seeing shadowy areas in your central vision or experiencing unusually fuzzy or distorted vision. Aside from possible links to a gene deficiency, the exact causes of age-related macular degeneration are still unknown. The dry form of AND may result from the aging and thinning of macular tissues, depositing of pigment in the macula, or a combination of the two processes. With wet AND, new blood vessels grow (neovascularization) beneath the retina and leak blood and fluid. This leakage causes retinal cells to die and creates blind spots in central vision. Other risk factors for AND include having a family member with AMD, smoking, high blood pressure, lighter eye color, farsightedness, and obesity. Some researchers believe that over-exposure to sunlight also may be a contributing factor in development of AMD, but this theory has not been proven conclusively. High levels of dietary fat also may be a risk factor for developing AMD.

Cytotoxicity of oxidized LDL has been reported in aortic endothelial cells (13) and retinal pigment epithelial (RPE) cells (14), with oxLDL inhibiting phagocytosis of rod outer segment membranes. Rodriguez et al (10) recently described that the cytotoxicity of oxidized LDL in cultured RPE cells is dependent on the formation of 7-ketocholesterol.

Therapeutic Uses of the Invention

The invention provides for treatment, amelioration or prevention of cholesterol-related diseases and disorders by administration of a therapeutic agent. Such agents include but are not limited to: C27 metabolites or derivatives of lanosterol, zymosterol or desmosterol, agents which mimic or are analogs of C27 metabolites or derivatives of lanosterol, zymosterol or desmosterol, agents able to act as antagonists of C27 metabolites or derivatives of lanosterol, zymosterol or desmosterol, sterols which have the formula Formula 1, agents which promote or prevent expression and/or activity of sterol 27-hydroxylase, agents which modulate the activity of sterol 27-hydroxylase, antibodies able to bind to or recognize C27 metabolites or derivatives of lanosterol, zymosterol or desmosterol, antibodies able to inhibit the activity of C27 metabolites or derivatives of lanosterol, zymosterol or desmosterol.

Agents of the formula Formula 1 are sterols having the formula:

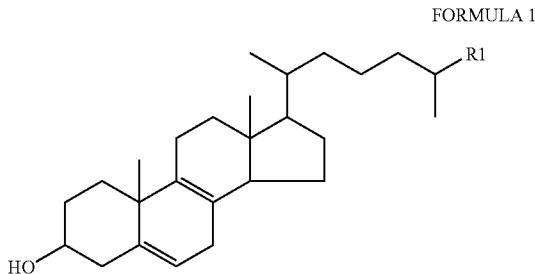

FORMULA 1 wherein R1 is selected from $CH_3$, $CH_2OH$, COOH, CO, CS, $CH_2$, CH, CHO;

or a pharmaceutically acceptable salt, solvate or prodrug thereof and isomers and stereoisomers thereof.

The invention further provides for modulation of gene expression, including and particularly via orphan nuclear receptors, by administration of a therapeutic agent. The invention provides for modulation of sperm capacitation or fertility by administration of a therapeutic agent. In addition, modulation of lipid disorders, particularly wherein the composition of plasma and cell membranes can be altered to provide treatment or amelioration of the disorder, is contemplated by administration of a therapeutic agent.

In a still further aspect, the invention provides a method for ameliorating, treating or preventing macular degeneration comprising modulating the expression or activity of CYP27A1 or sterol 27-hydroxylase. In one such aspect, a method is provided for ameliorating, treating or preventing macular degeneration in a mammal comprising administering to said mammal an agent which stimulates or enhances the expression or activity of CYP27A1 or sterol 27-hydroxylase. In a further aspect, a method is provided for ameliorating, treating or preventing macular degeneration in a mammal comprising increasing the 27-hydroxylation of cholesterol intermediates. A method is provided for ameliorating, treating or preventing macular degeneration in a mammal comprising increasing the 27-hydroxylation of 7-ketocholesterol in said mammal. In one such method, 27-hydroxyl-7-ketocholesterol is administered. In a further such aspect, a method is provided for ameliorating, treating or preventing macular degeneration in a mammal comprising administering to said mammal an agent which stimulates or enhances the expression or activity of hydroxysteroid sulphotransferase, particularly SULT2, particularly SULT2B1b. In a further aspect, a method is provided for ameliorating, treating or preventing macular degeneration in a mammal comprising increasing the sulfonation of cholesterol intermediates. A method is provided for ameliorating, treating or preventing macular degeneration in a mammal comprising increasing the sulfonation of 7-ketocholesterol in said mammal. In one such method, 7-ketocholesterol-3-sulfate is administered.

Therapeutic Compositions

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection by aerosol inhaler.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

The present invention also provides pharmaceutical compositions and formulations. Such compositions comprise a therapeutically effective amount of an agent, e.g., C27 metabolites or derivatives of lanosterol, zymosterol or desmosterol or an agent having the formula of Formula 1, and a pharmaceutically acceptable carrier. Such compositions may comprise a therapeutically effective amount of an agent capable of modulating, particularly stimulating, the expression or activity of CYP27A1 or sterol 27-hyrdoxylase. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of a disorder that can be ameliorated by administration of or the generation of C27 metabolites or derivatives of cholesterol or sterol intermediates, including of lanosterol, zymosterol or desmosterol or compounds having the formula of Formula 1 can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

Therapeutic Uses

The invention provides for treatment of diseases and disorders which can be ameliorated by a reduction of cholesterol synthesis, alteration of cholesterol metabolism, by administration of a therapeutic compound which is a C27 metabolite or derivative of lanosterol, zymosterol or desmosterol or an agent having the formula of Formula 1, a compound which is an antagonist of C27 metabolites or derivatives of lanosterol, zymosterol or desmosterol or an agent having the formula of Formula 1, and/or a compound able to alter the endogenous levels of C27 metabolites or derivatives of lanosterol, zymosterol or desmosterol or an agent having the formula of Formula 1. The invention provides for treatment of diseases and disorders which can be ameliorated by a reduction of cholesterol synthesis, alteration of cholesterol metabolism, by administration of a therapeutic compound which activates or stimulates expression or activity of CYP27A1 or sterol 27-hydroxylase. The invention provides for treatment of diseases and disorders which can be ameliorated by sulfonation of intermediates in cholesterol synthesis or by sulfonation of sterols, by administration of a therapeutic compound which is a sulfonated derivative of a sterol, particularly 3-sulfation, particularly 7-ketocholesterol-3-sulfate, a compound which is an agonist of sulfonated derivatives of sterols, particularly of 7-ketocholesterol-3-sulfate, and/or a compound able to alter the endogenous levels of or activity of hydroxysteroid sulfotrasferase, particularly SULT2, particularly SULT2B1b. The invention provides for treatment of macular degeneration by administration of a therapeutic compound which activates or stimulates expression or activity of CYP27A1 or sterol 27-hydroxylase or of hydroxysteroid sulfotrasferase, particularly SULT2, particularly SULT2B1b.

Compounds useful for this purpose include but are not limited to the C27 metabolites or derivatives of lanosterol, zymosterol or desmosterol or an agent having the formula of Formula 1 as described herein. Other compounds which are analogs or antagonists of C27 metabolites or derivatives of lanosterol, zymosterol or desmosterol or an agent having the formula of Formula 1, and/or compounds able to alter the endogenous levels of C27 metabolites or derivatives of lanosterol, zymosterol or desmosterol or an agent having the formula of Formula 1, can be identified by use of known in vitro assays, e.g., assays for the ability of a test compound to inhibit binding of C27 metabolites or derivatives of lanosterol, zymosterol or desmosterol or agents having the formula of Formula 1 to another protein or a binding partner, or to mimic or inhibit a known function of C27 metabolites or derivatives of lanosterol, zymosterol or desmosterol or agents having the formula of Formula 1. Preferably such inhibition is assayed in vitro or in cell culture, but genetic assays may also be employed. Preferably, suitable in vitro or in vivo assays are utilized to determine the effect of a specific compound and whether its administration is indicated for treatment of the affected tissue, as described in more detail below.

In a specific embodiment, a therapeutic agent of the invention is administered therapeutically or prophylactically to a subject in whom a decreased level of cholesterol biosynthesis is desired. Methods standard in the art can be employed to measure the decrease in cholesterol biosynthesis. In a particular embodiment, a therapeutic agent of the invention is administered therapeutically or prophylactically to a subject suffering from atherosclerosis. In a particular embodiment, a therapeutic agent of the invention is administered therapeutically or prophylactically to a subject suffering from coronary heart disease. In a particular embodiment, a therapeutic agent of the invention is administered therapeutically or prophylactically to a subject suffering from macular degeneration. In a particular embodiment, a therapeutic agent of the invention is administered therapeutically or prophylactically to a subject suffering from atheroma formation.

Screening Assays

The invention provides methods for identifying agents (e.g., candidate compounds or test compounds) that are: C27 metabolites or derivatives of lanosterol, zymosterol or desmosterol, agents which mimic or are analogs of C27 metabolites or derivatives of lanosterol, zymosterol or desmosterol, agents able to act as antagonists of C27 metabolites or derivatives of lanosterol, zymosterol or desmosterol, sterols which have the formula Formula 1, agents which promote or prevent expression and/or activity of sterol 27-hydroxylase, agents which modulate the activity of sterol 27-hydroxylase, antibodies able to bind to or recognize C27 metabolites or derivatives of lanosterol, zymosterol or desmosterol, antibodies able to inhibit the activity of C27 metabolites or derivatives of lanosterol, zymosterol or desmosterol capable of inhibiting the expression or activity of 27-hydroxy-7-dehydrocholesterol reductase. The invention further provides methods for identifying agents (e.g., candidate compounds or test compounds) that are: sulfonated metabolites or derivatives of steroids, particularly of 7-ketocholesterol; agents which mimic or are analogs of 7-ketocholesterol-3-sulfate; agents able to act as agonists of sulfonated metabolites or derivatives of sterols, particularly of 7-ketocholesterol; agents which promote or prevent expression and/or activity of hydroxysteroid sulphotransferase, particularly of SULT2B1b; agents which modulate the activity of hydroxysteroid sulphotransferase, particularly of SULT2B1b; antibodies able to bind to or recognize hydroxysteroid sulphotransferase, particularly of SULT2B1b; antibodies able to bind to or recognize sulfonated metabolites or derivatives of steroids, particularly of 7-ketocholesterol.

The expression and/or activity of sterol 27-hydroxylase (CYP27A1 can be assayed by methods known in the art, including by RT-PCR as described in Reiss et al (Reiss, A. B. et al (1997) J Lipid Res 38:1254-1260). CYP27A1 activity and/or expression has been reported to be modulated or regulated by transforming growth factor (TGF) $\beta 1$ (Hansson, M. et al. (2004) Biochem et Biophys Acta 1687:44-51), by overexpression of steroid acute regulatory protein (StAR) (Hall, E. A. et al. (2005) Biochim et Biophys Acta 1733(12-3):111-119), by the retinoid X receptor (RXR) ligand 9-cis-retinoic acid, as well as vitamin A and all-trans retinoic acid (ATRA), and PPAR (peroxisome-proliferator-activated receptor) gamma ligands (Quinn, C. M. et al. (2005) Biochem J 385(Pt 3):823-830; Langmann, T. et al. (2005) Biochem et Biophys Acta 1740(2): 155-161), by hepatic nuclear factor 4 (HNF4) alpha and by bile acids (Chen W. and Chiang J. Y. (2003) Gene 313:71-82), and by various hormones including growth hormone (GH), insulin-like growth factor-1 (IGF-1), dexamethasone, thyroxin ($T_4$) and PMA (Araya, Z. et al. (2003) Biochem J 372:529-534).

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (1990) Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

Phage display libraries may be used to screen potential ligands or sterol modulators. Their usefulness lies in the ability to screen, for example, a library displaying a billion different compounds with only a modest investment of time, money, and resources. For use of phage display libraries in a screening process, see, for instance, Kay et al., Methods, 240-246, 2001. An exemplary scheme for using phage display libraries to identify compounds that are C27 metabolites or derivatives of lanosterol, zymosterol or desmosterol, agents which mimic or are analogs of C27 metabolites or derivatives of lanosterol, zymosterol or desmosterol, or agents able to act as antagonists of C27 metabolites or derivatives of lanosterol, zymosterol or desmosterol, sterols which have the formula Formula 1, may be described as follows: initially, an aliquot of the library is introduced into microtiter plate wells that have previously been coated with target protein, e.g. an orphan nuclear receptor. After incubation (e.g. 2 hrs), the nonbinding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for the ligand or sterol may be obtained by performing ELISAs. One skilled in the art can easily perform these experiments. In one aspect, an orphan nuclear receptor molecule used for any of the assays may be selected from a recombinant orphan nuclear receptor protein, an orphan nuclear receptor fusion protein, an analog, derivative, or mimic thereof. In a preferred aspect, orphan nuclear receptor is a recombinant orphan nuclear receptor protein.

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; GRAS libraries; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

In one embodiment, agents that modulate C27 metabolites or derivatives of lanosterol, zymosterol or desmosterol, analogs thereof or sterols which have the formula Formula 1 are identified in a cell-free assay system. In accordance with this embodiment, a native or endogenous C27 metabolite or derivative of lanosterol, zymosterol or desmosterol, analog thereof or sterol having the formula Formula 1 is contacted with a candidate compound or a control compound and the ability of the candidate compound to inhibit the activity of said C27 metabolite or derivative of lanosterol, zymosterol or desmosterol, analog thereof or sterol having the formula Formula 1 is determined. If desired, this assay may be used to screen a plurality (e.g. a library) of candidate compounds. In more specific embodiments, the C27 metabolite or derivative of lanosterol, zymosterol or desmosterol, analog thereof or sterol having the formula Formula 1 is first immobilized, by, for example, contacting with an immobilized antibody which specifically recognizes and binds it, or by contacting a purified preparation thereof with a surface designed to bind it. Alternatively, sterol 27-hydroxylase may be first immobilized, by, for example, contacting with an immobilized antibody which specifically recognizes and binds it, or by contacting a purified preparation thereof with a surface designed to bind it. The sterol 27-hydroxylase may be partially or completely purified (e.g., partially or completely free of other polypeptides) or part of a cell lysate. Further, the enzyme may be a fusion protein comprising the enzyme and a domain such as glutathionine-S-transferase. Alternatively, the enzyme may be biotinylated using techniques well known to those of skill in the art (e.g., biotinylation kit, Pierce Chemicals; Rockford, Ill.). The ability of the candidate compound to be metabolized by sterol 27-hydroxylase can be determined by methods known to those of skill in the art.

In another embodiment, agents that modulate C27 metabolites or derivatives of lanosterol, zymosterol or desmosterol, analogs thereof or sterols which have the formula Formula 1 are identified in a cell-based assay system. In accordance with one example of this embodiment, cells containing C27 metabolites or derivatives of lanosterol, zymosterol or desmosterol, analogs thereof or sterols which have the formula Formula 1 are contacted with a candidate compound or a control compound and the ability of the candidate compound to modulate the activity of the C27 metabolites or derivatives of lanosterol, zymosterol or desmosterol, analogs thereof or sterols which have the formula Formula 1 is determined. In accordance with a further example of this embodiment, cells expressing sterol 27-hydroxylase activity are contacted with a candidate compound or a control compound and the ability of the candidate compound to modulate the enzyme activity is determined. If desired, this assay may be used to screen a plurality (e.g. a library) of candidate compounds. The cell, for example, can be of prokaryotic origin (e.g., *E. coli*) or eukaryotic origin (e.g., yeast or mammalian). Further, the cells can express sterol 27-hydroxylase endogenously or be genetically engineered to express the enzyme. In certain instances, the enzyme or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between the enzyme and a candidate compound. The ability of the candidate compound to modulate the activity of C27 metabolites or derivatives of lanosterol, zymosterol or desmosterol, analogs thereof or sterols which have the formula Formula 1 or of sterol 27-hydroxylase can be determined by methods known to those of skill in the art.

In another embodiment, agents that modulate the activity of a C27 metabolite or derivative of lanosterol, zymosterol or desmosterol, analog thereof or sterol having the formula Formula 1 are identified by contacting a preparation containing the sterol, or cells (e.g., prokaryotic or eukaryotic cells) expressing the sterol with a test compound or a control compound and determining the ability of the test compound to inhibit the activity of the C27 metabolite or derivatives of lanosterol, zymosterol or desmosterol, analog thereof or sterol having the formula Formula 1. The activity of the sterol can be assessed by detecting induction of a cellular signal transduction pathway of sterol (e.g., downstream metabolites) (e.g., 27-hydroxycholesterol), detecting catalytic or enzymatic activity of the target on a suitable substrate, detecting the induction of a reporter gene, or detecting a cellular response. Based on the present description, techniques known to those of skill in the art can be used for measuring these activities (see, e.g., U.S. Pat. No. 5,401,639, which is incorporated herein by reference). The candidate compound can then be identified as a inhibitor of the activity of 27-hydroxy-7-dehydrocholesterol reductase by comparing the effects of the candidate compound to the control compound. Suitable control compounds include phosphate buffered saline (PBS) and normal saline (NS).

In another embodiment, agents that inhibit the expression, activity or both the expression and activity of C27 metabolites or derivatives of lanosterol, zymosterol or desmosterol, analogs thereof or sterols which have the formula Formula 1 are identified in an animal model. Examples of suitable animals include, but are not limited to, mice, rats, rabbits, monkeys, guinea pigs, dogs and cats. In specific embodiments, the animal used represent a model of human cholesterol synthesis. In accordance with this embodiment, the test compound or a control compound is administered (e.g., orally, rectally or parenterally such as intraperitoneally or intravenously) to a suitable animal and the effect on the expression, activity or both expression and activity of C27 metabolites or derivatives of lanosterol, zymosterol or desmosterol, analogs thereof or sterols which have the formula Formula 1 is determined. Changes in the activity or expression of C27 metabolites or derivatives of lanosterol, zymosterol or desmosterol, analogs thereof or sterols which have the formula Formula 1 can be assessed by the methods outlined above.

Therapeutic Agent Antibodies

Also, antibodies including both polyclonal and monoclonal antibodies, and drugs that modulate the production or activity of the C27 metabolites or derivatives of lanosterol, zymosterol or desmosterol, analogs thereof, or agents having the formula of Formula 1 may possess certain diagnostic applications and may for example, be utilized for the purpose of detecting and/or measuring conditions such as cholesterol synthesis or metabolism, sterol constituents in animals or animal cells, or gene expression. For example, the C27 metabolites or derivatives of lanosterol, zymosterol or desmosterol or agents having the formula of Formula 1 may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the C27 metabolites or derivatives of lanosterol, zymosterol or desmosterol or agents having the formula of Formula 1 of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against the therapeutic agents can be screened for various properties; i.e., isotype, epitope, affinity, etc. Of particular interest are monoclonal antibodies that neutralize the activity of the C27 metabolites or derivatives of lanosterol, zymosterol or desmosterol or agents having the formula of Formula 1. Such monoclonals can be readily identified in activity assays. Preferably, the antibody used in the diagnostic methods of this invention is an affinity purified polyclonal antibody. More preferably, the antibody is a monoclonal antibody (mAb). In addition, it is preferable for the antibody molecules used herein be in the form of Fab, Fab', F(ab')$_2$ or F(v) portions of whole antibody molecules.

In one embodiment wherein inhibition of the C27 metabolites or derivatives of lanosterol, zymosterol or desmosterol or agents having the formula of Formula 1 is desirable, one or more antibodies each specifically binding thereto are administered alone or in combination with one or more additional therapeutic compounds or treatments.

Preferably, a biological product such as an antibody is allogeneic to the subject to which it is administered (e.g. to ameliorate symptoms or to retard onset or progression).

Antisense Nucleic Acids and Ribozymes

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into cells producing the C27 metabolites or derivatives of the invention. Antisense methods have been used to inhibit the expression of many genes in vitro (Marcus-Sekura, 1988; Hambor et al., 1988).

The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The invention further provides pharmaceutical compositions comprising an effective amount of the antisense nucleic acid of the invention in a pharmaceutically acceptable carrier, as described infra.

In another embodiment, the invention provides methods for inhibiting the expression of a nucleic acid sequence, including the sequence of a gene whose expression is activated in the presence or by a C27 metabolite or derivatives of lanosterol, zymosterol or desmosterol or agent having the formula of Formula 1, in a prokaryotic or eukaryotic cell comprising providing the cell with an effective amount of a composition comprising an antisense nucleic acid of the invention. In addition the sequence of the orphan receptor for which the C27 metabolites or derivatives of lanosterol, zymosterol or desmosterol or agents having the formula of Formula 1 is the ligand(s) may be targeted by antisense.

The antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. The oligonucleotide can be modified at the base moiety, sugar moiety, or phosphate backbone. The oligonucleotide may include other appended groups such as peptides; agents that facilitate transport across the cell membrane (see, e.g., Letsinger et al. (1989) Proc. Natl. Acad. Sci. USA 86:6553-6556; Lemaitre et al. (1987) Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988); hybridization-triggered cleavage agents (see, e.g., Krol et al. (1988) BioTechniques 6:958-976) or intercalating agents (see, e.g., Zon (1988) Pharm. Res. 5:539-549).

In a preferred aspect of the invention, an antisense oligonucleotide is provided, preferably of single-stranded DNA. The oligonucleotide may be modified at any position on its structure with substituents generally known in the art.

The antisense oligonucleotide may comprise at least one of the following modified base moieties: 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, and other base analogs. In another embodiment, the oligonucleotide comprises at least one modified sugar moiety, e.g., one of the following sugar moieties: arabinose, 2-fluoroarabinose, xylulose, and hexose.

In yet another embodiment, the oligonucleotide comprises at least one of the following modified phosphate backbones: a phosphorothioate, a phosphorodithioate, a phosphoramidothioate, a phosphoramidate, a phosphordiamidate, a methylphosphonate, an alkyl phosphotriester, a formacetal, or an analog of formacetal.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641).

The oligonucleotide may be conjugated to another molecule, e.g., a peptide, hybridization triggered cross-linking agent, transport agent, or hybridization-triggered cleavage agent.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448-7451).

In a specific embodiment, the antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding, for instance, an orphan nuclear receptor antisense nucleic acid or a sterol 27-hydroxylase antisense nucleic acid. Such a vector can remain episomal or become chromosomally integrated, as long as it can be transcribed to produce the desired antisense RNA. Such vectors can be constructed by recombinant DNA technology standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Examples of such promoters are outlined above.

The antisense nucleic acids of the invention comprise a sequence complementary to at least a portion of an RNA transcript of a gene. However, absolute complementarity, although preferred, is not required. A sequence "complementary to at least a portion of an RNA," as referred to herein, means a sequence having sufficient complementarity to be able to hybridize under stringent conditions (e.g., highly stringent conditions comprising hybridization in 7% sodium dodecyl sulfate (SDS), 1 mM EDTA at 65° C. and washing in 0.1×SSC/0.1% SDS at 68° C., or moderately stringent conditions comprising washing in 0.2×SSC/0.1% SDS at 42° C.)

with the RNA, forming a stable duplex; in the case of double-stranded 27-hydroxy-7-dehydrocholesterol reductase antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA e it may contain and still form a stable duplex (or triplex, as the case may be). One skilled in the art can ascertain a tolerable degree of mismatch by use of standard procedures to determine the melting point of the hybridized complex.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated. Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

In another embodiment, cholesterol-related disorders may be ameliorated or gene expression may be modulated by decreasing the level of a C27 metabolites or derivatives of lanosterol, zymosterol or desmosterol or agents having the formula of Formula 1 activity by using gene sequences encoding the sterol 27-hydroxylase enzyme in conjunction with well-known gene "knock-out," ribozyme or triple helix methods to decrease gene expression of sterol 27-hydroxylase. Alternatively, expression of a gene which is modulated by interaction of a ligand with its receptor may be altered using gene sequences encoding this target gene in gene "knock-out," ribozyme or triple helix methods to decrease gene expression thereof. In this approach ribozyme or triple helix molecules are used to modulate the activity, expression or synthesis of the encoding gene, and thus to ameliorate the symptoms of cholesterol-related disease. Such molecules may be designed to reduce or inhibit expression of a mutant or non-mutant target gene. Techniques for the production and use of such molecules are well known to those of skill in the art.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLES

The following examples are put forth so as to provide those of ordinary skill in the art with a complete disclosure and description of how to make and use the therapeutic methods of the invention and compounds and pharmaceutical compositions, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Summary

A major biologic role of the ubiquitous mitochondrial P 450 enzyme CYP 27A1 is the generation of ligands such as 27-hydroxycholesterol and 3β-hydroxy-5-cholestenoic acid, which regulate the expression of nuclear receptors that govern many aspects of cholesterol homeostasis. We now report that sterol intermediates in cholesterol synthesis, beginning with the initial post-cyclization sterol, lanosterol, continuing with zymosterol, and ending with desmosterol are also substrates for the enzyme. Using the human enzyme expressed in E. Coli, we characterized the retention times and major mass fragments of these novel metabolites.

Although sequestration of the enzyme in the inner mitochondrial membrane and normal subcellular organization may restrict the proportion of these and other intermediates in cholesterol synthesis that undergo side chain oxidation, disruption of compartmentalization can bypass cholesterol as the end product and give rise to potent ligands that further modify gene expression. In addition, administration of these intermediates or their C27 hydroxylation products, or analogs or antagonists thereof, may result in and be utilized for the modification of gene expression or modulation of cholesterol metabolism, synthesis and cholestatic disease.

Introduction

Although the initial role of sterol 27-hydroxylase was thought to be restricted only to bile acid synthesis in the liver, cloning of the gene and studies of its tissue distribution implied a much broader biologic role (1,2). This implication is supported by the knowledge that the numerous mutations in the CYP27 A1 gene are associated with a variety of phenotypes ranging from peripheral neuropathies to marked cognitive impairment and to non-neurologic problems such as early cataracts and accelerated atherosclerosis (3). Although no relationship between phenotypic expression and mutant genotype is apparent (3), accelerated atherosclerosis has been linked to a reduction in reverse cholesterol transport attributable to the normal role of 27-hydroxycholesterol and 3β-hydroxy-5-cholestenoic acid in regulating LXR nuclear receptor expression and thus ABC A1-mediated transport (4,5).

Another ligand, 27-hydroxy-7-dehydrocholesterol, occurring in relatively large amount in Smith-Lemli-Opitz syndrome (SLOS), was recently identified and was found to be specific for LXRα (6). The occurrence of a 27-hydroxy derivative of a normal intermediate in cholesterol synthesis implies that other intermediates in cholesterol synthesis may also be substrates for the enzyme. Thus, a variety of novel ligands with different biologic effects can occur endogenously under physiologic or, more likely, pathophysiologic conditions. Because of the wide variety of endogenous sterols that are substrates for CYP 27 A1, it becomes apparent that normal subcellular compartmentalization and organization is essential for directing the flow of these intermediates to their normal end products.

Materials and Methods

Materials.

Lanosterol, zymosterol, desmosterol and cholesterol were purchased from Steraloids (Newport, R.I.), Sigma (ST Louis, Mo.) or Research Plus (Raritan, N.J.). Each compound gave a characteristic spectrum by GLC-MS analysis. The 7-dehydro-cholesterol was a gift from Dr. Forbes Porter and was found to be essentially cholesterol-free.

Enzyme Incubations.

Recombinant human P450 27A1, recombinant bovine adrenodoxin (Adx), and recombinant bovine adrenodoxin reductase (Adr) were expressed and purified as described previously (7). P450 27A1 with a heme content of 17.6 nmol/mg protein and showing a single band upon silver-stained SDS-polyacrylamide gel electrophoresis, and Adr and Adx with the spectral purity indexes of 7.5 ($A_{278}/A_{450}$) and 0.95 ($A_{414}/A_{276}$), respectively, were used for enzymatic assays. Adr and Adx are considered to be pure with the spectral purity indexes beginning from 7.5 for Adr and 0.86 for Adx (8).

P450 27A1 activities using cholesterol, desmosterol, zymosterol, lanosterol, or 7-dehydroxycholesterol as the substrate were assayed in 40 mM phosphate buffer, pH 7.4. Stock solutions (10 mM) of cholesterol, desmosterol, zymosterol, and 7-dihydroxycholesterol were prepared using 45% aqueous solution of 2-hydroxypropyl-β-cyclodextrin. Reaction mixtures (1 ml) contained 0.065 nmol of P450 27A1, 0.33 nmol of Adr, 1.3 nmol of Adx, and 25 nmol of substrate, Lanosterol was dissolved in methyl-β-cyclodextrin (Sigma, St. Louis, Mo.) and the reaction mixture contained 25 nmol substrate, 0.3 nmol enzyme, 1.5 nmol Adr and 6.5 nmol Adx. Enzymatic assays, initiated by addition of 1 μmol of NADPH, were carried out at 37° C. for different time intervals, and were terminated by adding 1 ml of either $CH_2Cl_2$ or $CH_2Cl_2$ that contained coprostanol. After extraction, the steroid were taken to dryness. In some studies deuterated 27-hydroxycholesterol (9) was used as an internal standard.

Rates of catalysis of the different substrates compared with that of cholesterol and 7-dehydrocholesterol, known substrates for the enzyme, were determined using two different approaches. For zymosterol and desmosterol, the rate of diol formation was determined at 2.5, 5.0, and 10 min by removing aliquots and adding deuterated 27-hydroxycholesterol as an internal standard. The m/z 454 area was then compared with the m/z=462 area at each time interval. Because authentic standards are not available for constructing standard curves, it was assumed that the area/mass ratios for deuterated 27-hydroxycholesterol, zymosterol and desmosterol were equal. A second approach was to quantify the rate of disappearance of substrate using coprostanol added at the end of the incubation period. In all studies a parallel incubation with the omission of adrenodoxin reductase served as a control.

GLC-MS Analyses.

The trimethylsilyl ethers were prepared using MSTFA, (Pierce, Rockford, Ill.). Methyl esters were prepared using freshly distilled diazomethane. GLC-MS analyses were done on a Shimidzu GLC 17A instrument attached to a Model 5000 mass detector. Samples were injected in the split-mode onto a ZB-1701, 30 m×0.25 mm×0.15 μm capillary column (Phenomenex, Torrance, Calif.) and temperature programming at 1° C. beginning at 240° C.

Results

Metabolites of lanosterol, zymosterol, and desmosterol were detected in a SIM program using the calculated molecular ion of the 27-diol and the $C_{27}$ acid metabolites of each of the substrates (TABLE 1). For comparison, cholesterol and 7-dehydrocholesterol, known substrates for the enzyme (10, 11), were also studied. As shown in Table 1, each substrate yielded two peaks with different retention times. These peaks were present only in incubations containing all the components of the mitochondrial electron transfer chain.

TABLE 1

Molecular ion, major fragment, and retention time of metabolites of lanosterol, zymosterol, desmosterol, 7-dehydrocholesterol, and cholesterol after incubation with CYP27A1

| | Metabolites | | | | | |
|---|---|---|---|---|---|---|
| | $C_{27}$ Diols[a] | | | $C_{27}$ Acids[a] | | |
| Substrate | mol ion | frag | r.t (min) | mol ion | frag | r.t (min) |
| Lanolsterol | 586.7 | 481.7[b] | 31.7 | 542.7 | 437.7 | 35.7 |
| Zymosterol | | | 27.1 | | | 32.5 |
| Desmosterol | 544.3 | 454.3[c] | 26.3 | 500.3 | 410.3 | 28.2 |
| 7-Dehydrochol. | | | 27.4 | | | 29.3 |
| Cholesterol | 546.3 | 456.3 | 25.4 | 502.3 | 412.3 | 27.7 |

[a]Diols calculated as di-trimethyl silyl ether, Acids calculated as methyl ester + trimethyl silyl ether.
[b]Loss of methyl group from $C_4$ with silyl ether + water (15 + 72 + 18).
[c]Loss of one silyl group + water (72 + 18).

The initial rates of 27-diol formation for zymosterol and desmosterol compared with that of known substrates of the enzyme were determined in aliquots taken at 2.5, 5, and 10 min (TABLE 2). The ratio of the areas of m/z=454 to m/z=462 (deuterated 27-hydroxycholesterol) added at the end of each time period increased progressively.

TABLE 2

Rates of synthesis of the 27-diol metabolites of $C_{27}$ sterols

| | Synthesis rate (ng/min)[a] | | | Total |
|---|---|---|---|---|
| Substrate | 0-2.5 | 2.5-5.0 | 5.0-10 | ng/10 min |
| Cholesterol | 80 | 75 | 53 | 534 |
| 7-Dehydrocholesterol | 24 | 54 | 11 | 107 |
| Zymosterol | 9 | 14 | 10 | 97 |
| Desmosterol | 3 | 8 | 9 | 85 |

[a]Calculated from the area ratios of either m/z = 456 (cholesterol) or m/z = 454 (7-dehydrocholesterol, zymosterol, and desmosterol) to the deuterated internal standard m/z = 462.

TABLE 3 indicates the percent of zymosterol, desmosterol, and lanosterol that was metabolized compared with that of cholesterol and 7-dehydrocholesterol using coprostanol (m/z=370) as an internal standard and (−) adrenodoxin reductase as a control.

TABLE 3

Relative rates of $C_{27}$ hydroxylation of different sterols

| Substrate | Adrenodoxin reductase | Sterol/int std ratio | Percent metabolized[a] |
|---|---|---|---|
| Cholesterol | (−) | 0.98 | 22 |
| Cholesterol | + | 0.76 | |
| 7-Dehydrocholesterol | (−) | 0.95 | 32 |
| 7-Dehydrocholesterol | + | 0.65 | |
| Desmosterol | (−) | 0.12 | 25 |
| Desmosterol | + | 0.09 | |
| Lanosterol | (−) | 1.1 | 15 |
| Lanosterol | + | 0.93 | |

TABLE 3-continued

Relative rates of $C_{27}$ hydroxylation of different sterols

| Substrate | Adrenodoxin reductase | Sterol/int std ratio | Percent metabolized[a] |
|---|---|---|---|
| Lanosterol | (−) | 0.12 | 17 |
| Lanosterol | + | 0.10 | |

[a]Calculated from the disappearance of substrate at 20 min using the ratio of sterol/int std for incubations not containing adrenodoxin reductase as the control.

Figure 4:
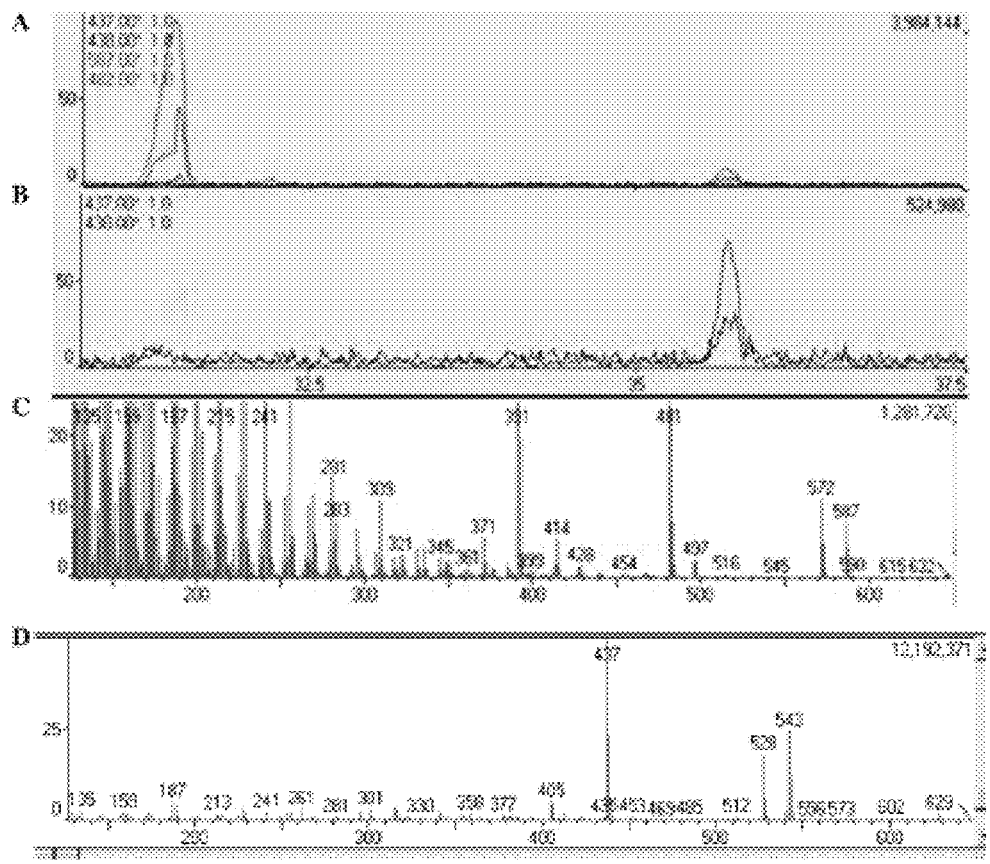
FIG. 4A-D depicts gas-liquid chromatographic-mass spectrographic (GLC-MS) analysis of metabolites of lanosterol. The top panel (A) indicates the ion monitoring program utilized to detect the diol (m/z=586.7, 481.7) and acidic metabolite (m/z=542.7, 437.7) of lanosterol. Because the acidic metabolite is much less, the peak is barely seen at 36 min but by monitoring only m/z=437, 438 it becomes much more identifiable as shown in (B). The full spectrum of lanosterol-27 diol is shown in (C). The molecular ion of the di-methyl silyl ether, m/z=587 is present together with a prominent m/z=572 indicating loss of a methul group (−15) probably from the $C_4$ carbon. Allowing for the 1 mass unit variation of the instrument, the m/z=391 represents the simultaneous loss of a methyl+silyl group (15+90) and the prominent m/z=481 and 391 fragments represent the successive loss of sialyl ethers from m/z=572 establishing the presence of two hydroxyl groups on the metabolite. The bottom (D) illustrates the full spectrum of the $C_{27}$ acid metabolite. The expected molecular ion of the $C_{27}$ methyl ester and C3-O-silyl ether is present (m/z=543) together with a prominent m/z=528(−15).

FIG. 4 illustrates a typical GC-MS analysis. The top panel indicates the two metabolites of lanosterol that were detected. Because the area of the diol metabolite, retention time 31.7 min, is much greater than that of the acidic metabolite, retention time of 35.7 min, the latter it is not readily apparent until the m/z ions for the diol are not entered into the program, as shown in the middle panel. A sufficient amount of diol metabolite was obtained for a complete spectrum which establishes the presence of two hydroxyl groups on the metabolite (bottom panel). We are not aware of the existence of an authentic standard.

Discussion

Figure 1:
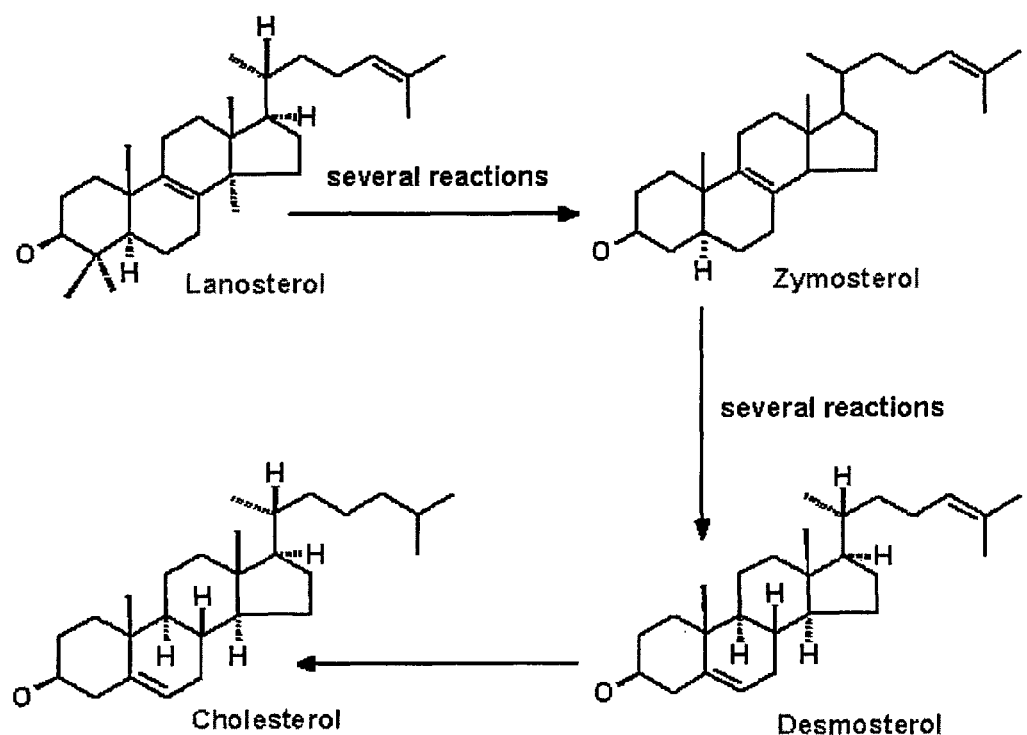
FIG. 1 depicts the conversion of lanosterol to cholesterol and their structures.
Figure 2:
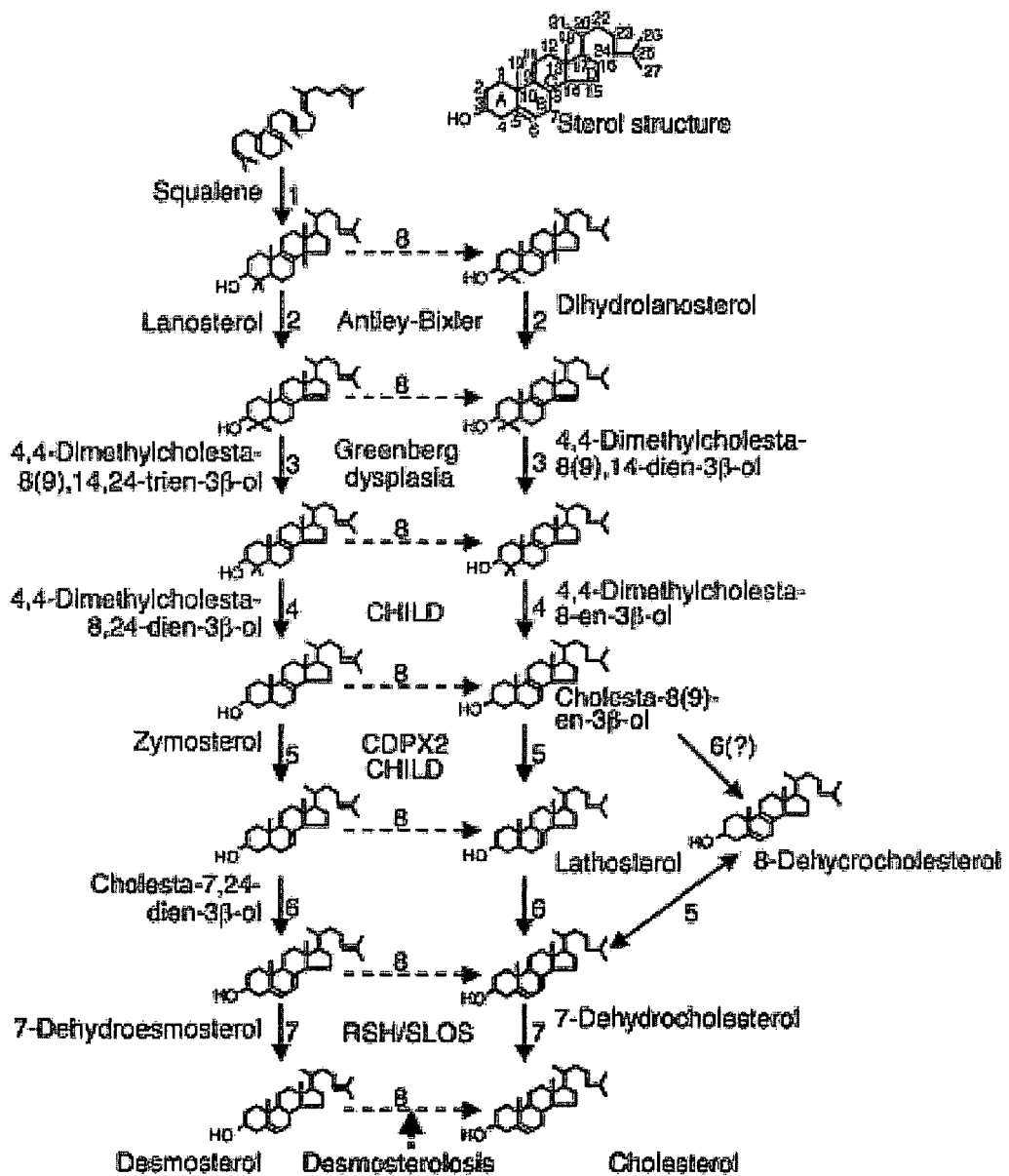
FIG. 2 depicts the cholesterol synthesis pathway from squalene to cholesterol, including intermediates from lanosterol to zymosterol to desmosterol. The sterol ring and carbon position numbering are shown on the top of the figure. Human malformation syndromes are indicated. Cholesterol is synthesized from squalene in a series of enzymatic reactions denoted by numbers: 1, squalene monooxygenase and squalene cyclase; 2, lanosterol 14-α-demethylase; 3, 3β-hydroxysterol $\Delta^{14}$-reductase; 4, C4 demethylation complex (C4-sterol methyloxidase, C4-sterol decaroxylase [NSDHL], and 3-ketoreductase); 5, 3β-hydroxysterol $\Delta^8,\Delta^7$-isomerase; 6, lathosterol 5-desaturase; 7, 3β-hydroxysterol $\Delta^7$-reductase; 8, 3β-hydroxysterol $\Delta^{24}$-reductase.
Figure 3:
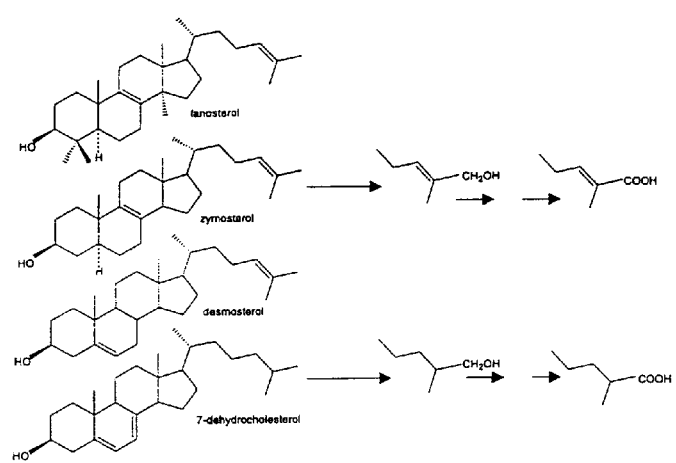
FIG. 3 depicts CYP27A1 catalyzed metabolism normal intermediates in cholesterol synthesis are substrates for the multifunctional P450 enzyme located on the inner mitochondrial membrane. The arrows → indicate that successive CYP27A1 catalyzed oxidations occur beginning with the $C_{27}$-diol and ending with the $C_{27}$-acid.

The data indicate that normal intermediates in cholesterol synthesis are substrates for CYP 27A1, a multifunctional mitochondrial P 450 enzyme (1,2). Each of these compounds represents new information with respect to the substrate specificity of the mitochondrial enzyme. Thus, finding that lanosterol, a C30 compound with a 5α-oriented sterol ring and methyl groups at $C_4$ and $C_{14}$ (FIG. 3) is a substrate greatly broadens our thinking in regard to the class of compounds that can be metabolized via side chain oxidation. Both zymosterol and desmosterol are $C_{27}$ sterols, the former has 5α sterol ring structure and the latter has an unsaturation on the side chain between $C_{24}$ and $C_{25}$. Although other normal intermediates that are generated in the pathway from lanosterol to desmosterol or to 7-dehydrocholesterol are not available for study, it is reasonable to think that many, if not all, can be substrates for the enzyme.

Using substrate disappearance (TABLE 3), it appears that the rate of metabolism of lanosterol is less than that of other substrates. Since both lanosterol and zymosterol have the same ring configuration, the difference can be attributed to the effect of the configuration of the additional methyl groups.

To evaluate the physiologic or pathophysiologic significance of these findings the major considerations are access to the enzyme site and the relative rates of catalysis compared with that of the known substrates, cholesterol and 7-dehydrocholesterol. The lack of authentic standards for the metabolites of lanosterol, zymosterol, and desmosterol precludes precise determination of the amount of each metabolite that is formed since standard curves cannot be constructed. For zymosterol and desmosterol, which have the same molecular weight as 7-dehydrocholesterol, it seemed reasonable to compare the rate of formation of the diol using the area of the m/z=454 fragment. To further evaluate the relative rates of catalysis we determined the rate of disappearance of substrate, which includes the formation of both the diol and acid metabolites. Thus the apparent difference between the rates of catalysis of cholesterol and 7-dehydrocholesterol can be attributed to differences in the amount of acid metabolites formed. It is known that a variety of conditions affect the proportion of the two metabolites (7,12).

Although the rates of catalysis for the intermediates in cholesterol synthesis may be less than that of cholesterol, they are comparable with the formation of the 27-hydroxy-7-dehydrocholesterol, previously found in incubations of 7-dehydrocholesterol with liver homogenates and recombinant P450 27A1 (10,11). More recently, 27-hydroxy-7-dehydrocholesterol was identified in the plasma of normal individuals and those with Smith-Lemli-Opitz syndrome (SLOS) in picomolar and micromolar amounts, respectively (6). The greater levels in plasma from SLOS patients than normal individuals can be attributed to the rise in cellular levels of 7-dehydrocholesterol because of the decreased conversion of 7-dehydrocholesterol to cholesterol. Based on this knowledge, it is likely that under physiologic conditions intermediates in cholesterol synthesis proceed almost entirely to cholesterol unless disruptions in the enzymatic process that raise their cellular concentrations occur.

However, determinants of access to the enzyme rather than an increase in cell concentration should also be considered. Although the enzyme is located on the matrix side of the inner mitochondrial membrane (13), it is known that the $C_{27}$ 7α-hydroxylated intermediates in bile acid synthesis in the liver, normally present in very low concentration in the cell (14), rapidly gain access to the enzyme which is required for normal bile acid synthesis. In contrast to its effect on cholesterol, access to the enzyme by these intermediates is not modulated by StAR protein expression (15). However, lack of 27-hydroxylase activity results in an increase in their cellular levels (14).

The subcellular mechanisms that normally distinguish between the $C_{27}$ intermediates in bile acid synthesis and the $C_{27}$ intermediates in cholesterol synthesis with respect to enzyme access are largely unknown. It seems reasonable to speculate that disruption of normal cellular organization, particularly events that increase mitochondrial permeability, can generate a variety of novel "oxysterol" ligands, derived from intermediates in cholesterol synthesis, which then alter gene expression and thus dominate the pathophysiological processes that occur.

References

1. Cali, J. J., and Russell, D. W. (1991) *J Biol Chem* 266, 7774-7778
2. Andersson, S., Davis, D. L., Dahlback, H., Jornvall, H., and Russell, D. W. (1989) *J Biol Chem* 264, 8222-8229
3. Verrips, A., Hoefsloot, L. H., Steenbergen, G. C., Theelen, J. P., Wevers, R. A., Gabreels, F. J., van Engelen, B. G., and van den Heuvel, L. P. (2000) *Brain* 123 (Pt 5), 908-919
4. Fu, X., Menke, J. G., Chen, Y., Zhou, G., MacNaul, K. L., Wright, S. D., Sparrow, C. P., and Lund, E. G. (2001) *J Biol Chem* 276, 38378-38387
5. Song, C., and Liao, S. (2000) *Endocrinology* 141, 4180-4184
6. Wassif C A, Y. J., Cui J, Porter F D, and Javitt, N B. (2003) *Steroids* 68(6), 497-502.
7. Pikuleva, I. A., Bjorkhem, I., and Waterman, M. R. (1997) *Arch Biochem Biophys* 343, 123-130
8. Kimura, T., Parcells, J. H., and Wang, H. P. (1978) *Methods Enzymol* 52, 132-142
9. Javitt, N. B., Kok, E., Lloyd, J., Benscath, A., and Field, F. H. (1982) *Biomed Mass Spectrom* 9, 61-63
10. Bjorkhem, I., Starck, L., Andersson, U., Lutjohann, D., von Bahr, S., Pikuleva, I., Babiker, A., and Diczfalusy, U. (2001) *J Lipid Res* 42, 366-371
11. Honda, A., Salen, G., Shefer, S., Batta, A. K., Honda, M., Xu, G., Tint, G. S., Matsuzaki, Y., Shoda, J., and Tanaka, N. (1999) *J Lipid Res* 40, 1520-1528
12. Pikuleva, I. A., Babiker, A., Waterman, M. R. and Bjorkhem, I. (1986) J. Biol. Chem. 18153-18160.

13. Miller, W. L. (1988) *Endocr Rev* 9, 295-318
14. Bjorkhem, I., Oftebro, H., Skrede, S., and Pedersen, J. I. (1981) *J Lipid Res* 22, 191-200
15. Sugawara, T., Lin, D., Holt, J. A., Martin, K. O., Javitt, N. B., Miller, W. L., and Strauss, J. F., 3rd. (1995) *Biochemistry* 34, 12506-12512

Example 2

The endoplasmic reticulum (ER) enzyme 3-hydroxy-3-methylglutaryl-CoA (HMG CoA) reductase produces mevalonate, a crucial intermediate in the synthesis of cholesterol and nonsterol isoprenoids. Mevalonate is converted to sterols and to other products, including the farnesyl and geranylgeranyl groups attached to proteins, directing them to membranes. HMG CoA reductase is subject to tight regulation by a multivalent feedback mechanism mediated by nonsterol and sterol end products of mevalonate metabolism. Excess sterols promote ubiquitination and subsequent degradation of reductase as part of this negative regulation feedback. Feedback control of cholesterol synthesis is mediated, in part, by sterol-induced binding of HMG CoA reductase to Insig proteins in the ER (Sever, N et al (2003) J Biol Chem 278(52):52479-52490). Binding leads to ubiquitination and proteosomal degradation of reductase (Song, B-L and DeBose-Boyd R A (2004) J Biol Chem 279(27):28798-28806).

It was determined whether intermediates in cholesterol synthesis promote ubiquitination of reductase in a permeabilized cell system. Lanosterol, the first intermediate in the cholesterol synthetic pathway, but not cholesterol itself, was found to potently stimulate ubiquitination of reductase. Of the sterols tested, only 25-hydroxycholesterol, lanosterol, 27-hydroxylanosterol, 7-keto-25-hydroxycholesterol, and 27-hydroxycholesterol stimulated ubiquitination of reductase in permeabilized cells (data not shown). In particular, 27-hydroxylanosterol strongly stimulated reductase ubiquitination, prompting the comparison of its ubiquitinating activity at lower concentrations to that of other positive sterols at 25 µM. It was found that 2.5 µM 27-hydroxylanosterol stimulated approximately equivalent levels of reductase ubiquitination as 25 µM lanosterol (data not shown). These results indicate that hydroxyl groups in the sterol side chain and methyl groups at the C4 and/or C14 positions are key determinants for recognition in the sterol-sensing phase of reductase degradation. The methyl and side chain hydroxyl groups of 27-hydroxylanosterol appear to act synergistically in promoting reductase ubiquitination.

Example 3

Biologic Effect of 27-hydroxylation of 7-ketocholesterol

The knowledge that 7-ketocholesterol normally circulates in human plasma (1), accumulates in atheroma (2-5), and perhaps other tissues, together with data that it is highly toxic in cell culture (6-9) has led to the concept that it may have a pathogenetic role in the development of age-related atheroma. More recently, studies by Rodriguez et al (10) have linked 7-ketocholesterol to cytotoxicity in retinal pigment epithelial cells and implicated 7-ketocholesterol as a cause of retinal pigment epithelial injury leading to macular degeneration.

Macular degeneration, often called AMD or ARMD (for age-related macular degeneration), is the leading cause of vision loss and blindness in Americans aged 65 and older. Because older people represent an increasingly larger percentage of the general population, vision loss associated with AMD is a growing problem. AMD is a degenerative condition of the macula, which is the part of the retina responsible for the sharp, central vision needed to read or drive. Because AMD affects the macula, central vision loss may occur. Macular degeneration is diagnosed as either dry (non-neovascular) or wet (neovascular). The dry form is more common than the wet, with about 85%-90% of AMD patients diagnosed with dry AMD. The wet form of the disease usually leads to more serious vision loss.

Macular degeneration produces a slow, or rarely, sudden painless loss of vision. Early signs of vision loss associated with AMD can include seeing shadowy areas in your central vision or experiencing unusually fuzzy or distorted vision. Aside from possible links to a gene deficiency, the exact causes of age-related macular degeneration are still unknown. The dry form of AMD may result from the aging and thinning of macular tissues, depositing of pigment in the macula, or a combination of the two processes. With wet AMD, new blood vessels grow (neovascularization) beneath the retina and leak blood and fluid. This leakage causes retinal cells to die and creates blind spots in central vision. Other risk factors for AMD include having a family member with AMD, smoking, high blood pressure, lighter eye color, farsightedness, and obesity. Some researchers believe that over-exposure to sunlight also may be a contributing factor in development of AMD, but this theory has not been proven conclusively. High levels of dietary fat also may be a risk factor for developing AMD.

Cytotoxicity of oxidized LDL has been reported in aortic endothelial cells (13) and retinal pigment epithelial (RPE) cells (14), with oxLDL inhibiting phagocytosis of rod outer segment membranes. As noted above, Rodriguez et al (10) recently described that the cytotoxicity of oxidized LDL in cultured RPE cells is dependent on the formation of 7-ketocholesterol.

We undertook to determine the effect of 27-hydroxylation of 7-ketocholesterol on the cytotoxic effect of 7-ketocholesterol. To test the general hypothesis that 27-hydroxylation of steroids markedly alters their biologic activity, the 27-hydroxy derivative of 7-ketocholesterol was synthesized from 27-hydrocholesterol using modifications of a previously published method (11). Its biologic effects on human retinal pigment epithelial cells (ARPE19) was compared to that of 7-ketocholesterol.

As shown in FIG. 5, the viability of retinal pigment epithelial cells maintained in the presence of 25 or 50 µmolar 7-ketocholesterol fell to 68% and 20% respectively. By contrast, retinal pigment epithelial cells maintained in the presence of 27-hydroxy-7-ketocholesterol had only a 10% reduction in viability compared to control.

Although the molecular mechanisms that cause loss of cell viability in the presence of 7-ketocholesterol and the modulation that occurs when the 27-hydroxy derivative is formed is under active study it is clear that activation of the CYP 27 catalyzed metabolic pathway markedly reduces the toxicity of 7-ketocholesterol.

A new class of therapeutic agents directed at upregulating the amount or activity of CYP 27A1 (12) can provide a novel approach to the prevention of atheroma formation and retinal pigment epithelial injury.

1. Dzeletovic, S., Breuer, O., Lund, E., and Diczfalusy, U. (1995) Determination of cholesterol oxidation products in human plasma by isotope dilution-mass spectrometry. *Anal Biochem* 225, 73-80
2. Hodis, H. N., Crawford, D. W., and Sevanian, A. (1991) Cholesterol feeding increases plasma and aortic tissue cholesterol oxide levels in parallel: further evidence for the role of cholesterol oxidation in atherosclerosis. *Atherosclerosis* 89, 117-126
3. Hulten, L. M., Lindmark, H., Diczfalusy, U., Bjorkhem, I., Ottosson, M., Liu, Y., Bondjers, G., and Wiklund, O. (1996) Oxysterols present in atherosclerotic tissue decrease the expression of lipoprotein lipase messenger RNA in human monocyte-derived macrophages. *J Clin Invest* 97, 461-468
4. Carpenter, K. L., Taylor, S. E., van der Veen, C., Williamson, B. K., Ballantine, J. A., and Mitchinson, M. J. (1995) Lipids and oxidised lipids in human atherosclerotic lesions at different stages of development. *Biochim Biophys Acta* 1256, 141-150
5. Garcia-Cruset, S., Carpenter, K. L., Guardiola, F., and Mitchinson, M. J. (1999) Oxysterols in cap and core of human advanced atherosclerotic lesions. *Free Radic Res* 30, 341-350
6. Santillan, G., Sarma, J. S., Pawlik, G., Rackl, A., Grenier, A., and Bing, R. J. (1980) Toxicity, pharmacokinetics, and cholesterol-inhibitory effect of 7-ketocholesterol. *Atherosclerosis* 35, 1-10
7. Naseem, S. M., and Heald, F. P. (1987) Cytotoxicity of cholesterol oxides and their effects on cholesterol metabolism in cultured human aortic smooth muscle cells. *Biochem Int* 14, 71-84
8. Clare, K., Hardwick, S. J., Carpenter, K. L., Weeratunge, N., and Mitchinson, M. J. (1995) Toxicity of oxysterols to human monocyte-macrophages. *Atherosclerosis* 118, 67-75
9. Ohtani, K., Miyabara, K., Okamoto, E., Kamei, M., and Matsui-Yuasa, I. (1996) Cytotoxicity of 7-ketocholesterol toward cultured rat hepatocytes and the effect of vitamin E. *Biosci Biotechnol Biochem* 60, 1989-1993
10. Rodriguez, I. R., Alam, S., and Lee, J. W. (2004) Cytotoxicity of oxidized low-density lipoprotein in cultured RPE cells is dependent on the formation of 7-ketocholesterol. *Invest Ophthalmol Vis Sci* 45, 2830-2837
11. Li, S., Pang, J., Wilson, W. K., and Schroepfer, G. J., Jr. (1999) Sterol synthesis. Preparation and characterization of fluorinated and deuterated analogs of oxygenated derivatives of cholesterol. *Chem Phys Lipids* 99, 33-71
12. Hansson, M., Wikvall, K., and Babiker, A. (2005) Regulation of sterol 27-hydroxylase in human monocyte-derived macrophages: up-regulation by transforming growth factor beta1. *Biochim Biophys Acta* 1687, 44-51
13. Cominacini, L. Pasinis, A. F. Garbin, U. et al. (2001) The binding of oxidized low density lipoprotein (ox-LDL) to ox-LDL receptor-1 reduces the intracellular concentration of nitric oxide in endothelial cells through an increased production of superoxide. *J Biol Chem* 276, 13750-13755
14. Hoppe, G., Marmorstein, A. D., Pennock, E. A. and Hoff, H. F. (2001) Oxidized low density lipoprotein-induced inhibition of processing of photoreceptor outer segments by RPE. *Invest Ophthalmol Vis Sci* 42, 2714-2720

Example 4

To assess the expression of apoproteins, particularly of Cyp27A1 enzyme, responsible for 27-hydroxylation of cholesterol and steroid compounds and intermediates, in the adult retina, RT-PCR was performed on cDNA from RNA isolated from both adult retina and adult PE/CH (pigment epithelium/choroids). RT-PCR was conducted using primers against ApoE, ApoA1, ApoA2, ApoA4, Cyp27A1. GAPDH was used as a control for expression. The results are shown in FIG. 6. Along with the expected GAPDH control, Cyp27A1 RNA is expressed in the retina and PE/CH cells. The primers and methods for RT-PCR for CYP27A1 were as described in Reiss et al (Reiss, A. B. et al (1997) J Lipid Res 38:1254-1260). This study confirms that Cyp27A1 is present and expressed in retina and PE/CH cells and available for modification and hydroxylation of steroid and cholesterol compounds and intermediates.

Example 5

As a follow up to the studies of Example 3, demonstrating that chemical modification of 7-ketocholesterol with 27-hydroxylation resulted in a negation of the cytotoxicity of 7-ketocholesterol compound in retinal pigment epithelial cells, the effect of 7-ketocholesterol sulfate (3-sulfate 7-ketocholesterol) on human retinal pigment epithelial cells (ARPE 19 cells) was assessed. Indeed, the sulfation modification of 7-ketocholesterol similarly maintained the viability of RPE cells in culture, while addition of 7-ketocholesterol resulted in little RPE cell survival. To prepare the 3-sulfate, 7-ketocholesterol was reacted with a 10% molar excess of pyridine/$SO_3$ complex (Sigma) both dissolved in pyridine and kept at 60° C. overnight. The final product was extracted into ethyl acetate/methanol and converted to the sodium salt. A single spot with an Rf=0.56 (7-ketocholesterol Rf=0.82) was obtained after development on a silica gel G plate using a solvent system of n-butanol:acetic acid:water 10:1:1 v/v/v. A single peak with the expected molecular ion was also obtained by HPLC-mass spectrometry. For cell culture the compounds were dissolved in 45% hydroxypropyl-beta-cyclodextrin at a concentration so that when 10 ul was added to the medium the final concentration of the ketocholesterol was 50 uM. The number of surviving cells was determined at 96 hr and expressed as a % of control. The results are depicted in FIG. 7.

Sulfation of 7-ketocholesterol, and of steroid and cholesterol compounds more generally, is mediated in vivo by hydroxysteroid sulfotransferase, most particularly, SULT2B1b. Cytosolic sulphotransferases transfer the sulpho moiety from the cofactor 5'-phosphoadenosine-3'-phosphosulphate (PAPS) to nucleophilic groups of xenobiotics and small endogenous compounds (such as hormones, steroids and neurotransmitters). This reaction often leads to products that can be excreted readily. All known cytosolic sulphotransferases are members of an enzyme/gene superfamily termed SULT. Different SULT forms substantially differ in their substrate specificity and tissue distribution. In humans, 10 SULT genes are known (for review see Glatt, H. et al. (2001) Mutat Res 482(1-2):27-40; Chapman, E. et al. (2004) Angew Chem Int Ed Engl 43(27):3526-3548). The SULT2 gene encodes two different enzyme forms due to the use of alternative first exons. Sulfotransferase 2B1b (SULT2B1b) is a member of SULT 2 gene family. SULT2B1a and SULT2B1b are transcribed from the same gene using different transcriptional start sites and contain different first exons as the result of alternative splicing. SULT2B1a and SULT2B1b are 350 and 365 amino acids in length, respectively (Her, C. et al. (1998) Genomics 53:284-95). SULT2B1b is selective for the sulfation of 3beta-hydroxysteroids such as dehydroepiandrosterone and pregnenolone as well as cholesterol. SULT2B1b produces cholesterol sulfotransferase, whereas SULT2B1a yields pregnenlone sulfotransferase (Fuda H et al. (2002) J Biol Chem 277(39):36161-36166). Sulfotransferases have been implicated in various pathophysiological processes and as a result interest in their targeting for therapeutic intervention has been generated. In humans, the biotransformation of cholesterol and its hydroxylated metabolites (oxysterols) by sulfonation is a fundamental process of importance. Both SLUT2 forms are expressed in skin, a tissue where cholesterol sulfonation plays an important and essential role in normal development of the skin barrier (Javitt, N B et al. (2001) Endocrinology 142(7):2978-2984). In addition, cholesterol sulfate influences blood clotting and fibrinolysis and, as a constituent of platelets, supports platelet aggregation. Expression of SLUT2B1b RNA has been assessed in platelets by RT-PCR (Yanai, H. et al. (2004) Circulation 109(1):92-96). High throughput methods for discovery of sulfotransferase modulators have been reported (Best, M. D. et al. (2004) Chembiocem 5(6):811-819; Brik, A. et al. (2005) Bioorg Med Chem 13(15):4622-4626). It is clear that activation of the SULT2 pathway, particularly SULT2B1b, markedly reduces the toxicity of 7-ketocholesterol.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The invention claimed is:

1. A screening method for identifying agent compounds capable of stimulating or inhibiting the activity of C27 metabolites of lanosterol, zymosterol or desmosterol selected from the group consisting of lanosterol-27 diol, lanosterol-27 acid, zymosterol-27 diol, zymosterol-27 acid, desmosterol-27 diol, desmosterol-27 acid, and sterols which have the Formula 1,

FORMULA 1

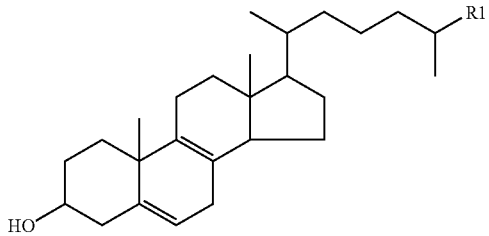

wherein R1 is selected from CH$_3$, COOH, CO, CS, CH$_2$, CH, and CHO, comprising measuring the activity of said C27 metabolite of lanosterol, zymosterol or desmosterol in the presence of a test compound, wherein a compound which stimulates said activity relative to a control is identified as a compound capable of increasing the activity of said C27 metabolite of lanosterol, zymosterol or desmosterol and a compound which inhibits said activity relative to a control is identified as a compound capable of reducing the activity of said C27 metabolite of lanosterol, zymosterol or desmosterol, wherein the activity is measured using lanosterol, zymosterol and/or desmosterol as substrates and the rates of 27-diol and/or 27-acid formation are determined.

2. A screening method for identifying agent compounds capable of inhibiting the activity of C27 metabolites of lanosterol, zymosterol or desmosterol selected from the group consisting of lanosterol-27 diol, lanosterol-27 acid, zymosterol-27 diol, zymosterol-27 acid, desmosterol-27 diol, desmosterol-27 acid, and sterols which have the Formula 1,

FORMULA 1

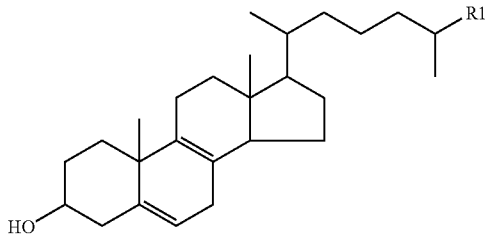

wherein R1 is selected from CH$_3$, COOH, CO, CS, CH$_2$, CH, and CHO, comprising measuring the activity of said C27 metabolite of lanosterol, zymosterol or desmosterol in the presence of a test compound, wherein a compound which reduces said activity relative to a control is identified as a compound capable of inhibiting the activity of said C27 metabolite of lanosterol, zymosterol or desmosterol, wherein the activity is measured using lanosterol, zymosterol and/or desmosterol as substrates and the rates of 27-diol and/or 27-acid formation are determined.

3. A screening method for identifying agent compounds capable of activating or enhancing the activity of C27 metabolites of lanosterol, zymosterol or desmosterol selected from the group consisting of lanosterol-27 diol, lanosterol-27 acid, zymosterol-27 diol, zymosterol-27 acid, desmosterol-27 diol, desmosterol-27 acid, and sterols which have the Formula 1,

FORMULA 1 wherein R1 is selected from CH$_3$, COOH, CO, CS, CH$_2$, CH, and CHO, comprising measuring the activity of said C27 metabolite of lanosterol, zymosterol or desmosterol in the presence of a test compound, wherein a compound which activates or enhances said activity relative to a control is identified as a compound capable of activating or enhancing the activity of said C27 metabolite of lanosterol, zymosterol or desmosterol, wherein the activity is measured using lanosterol, zymosterol and/or desmosterol as substrates and the rates of 27-diol and/or 27-acid formation are determined.

4. A screening method for identifying agent compounds capable of mimicking the activity of C27 metabolites of lanosterol, zymosterol or desmosterol selected from the group consisting of lanosterol-27 diol, lanosterol-27 acid, zymosterol-27 diol, zymosterol-27 acid, desmosterol-27 diol, desmosterol-27 acid, and sterols which have the Formula 1,

FORMULA 1

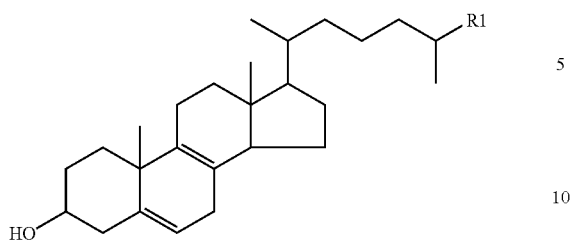

wherein R1 is selected from $CH_3$, COOH, CO CS, $CH_2$, CH, and CHO,
comprising screening for or measuring a known activity of said C27 metabolite of lanosterol, zymosterol or desmosterol in the presence of a test compound, wherein a compound which mimics said activity relative to a control is identified as a compound capable of mimicking the activity of said C27 metabolite of lanosterol, zymosterol or desmosterol, wherein the activity is measured using lanosterol, zymosterol and/or desmosterol as substrates and the rates of 27-diol and/or 27-acid formation are determined.

* * * * *